United States Patent
Zaslavsky et al.

(10) Patent No.: US 11,690,602 B2
(45) Date of Patent: Jul. 4, 2023

(54) METHODS AND APPARATUS FOR TELE-MEDICINE

(71) Applicant: BFLY OPERATIONS, INC., Burlington, MA (US)

(72) Inventors: Maxim Zaslavsky, San Diego, CA (US); Matthew de Jonge, New York, NY (US); Tomer Gafner, Forest Hills, NY (US); Eamon Duffy, New Haven, CT (US); Jonathan M. Rothberg, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 51 days.

(21) Appl. No.: 16/285,573

(22) Filed: Feb. 26, 2019

(65) Prior Publication Data

US 2019/0261957 A1 Aug. 29, 2019

Related U.S. Application Data

(60) Provisional application No. 62/646,333, filed on Mar. 21, 2018, provisional application No. 62/636,127, filed on Feb. 27, 2018.

(51) Int. Cl.
*G16H 40/67* (2018.01)
*A61B 8/00* (2006.01)
(Continued)

(52) U.S. Cl.
CPC .............. *A61B 8/54* (2013.01); *A61B 8/4263* (2013.01); *A61B 8/463* (2013.01); *A61B 8/465* (2013.01);
(Continued)

(58) Field of Classification Search
CPC combination set(s) only.
See application file for complete search history.

(56) References Cited

U.S. PATENT DOCUMENTS 5,922,018 A 7/1999 Sarvazyan
7,912,733 B2 * 3/2011 Clements ............... G16H 10/60
705/2

(Continued)

OTHER PUBLICATIONS

International Preliminary Report on Patentability dated Sep. 3, 2020 in connection with International Application No. PCT/US2019/019551.

(Continued)

*Primary Examiner* — Hien L Duong
(74) *Attorney, Agent, or Firm* — Carter, DeLuca & Farrell LLP

(57) ABSTRACT

Aspects of the technology described herein relate to ultrasound data collection using tele-medicine. An instructor electronic device may generate for display an instructor augmented reality interface and receive, on the instructor augmented reality interface, an instruction for moving an ultrasound imaging device. The instructor augmented reality interface may include a video showing the ultrasound imaging device and a superposition of arrows on the video, where each of the arrows corresponds to a possible instruction for moving the ultrasound imaging device. A user electronic device may receive, from the instructor electronic device, an instruction for moving an ultrasound imaging device, and generate for display, on a user augmented reality interface shown on the user electronic device, the instruction for moving the ultrasound imaging device. The user augmented reality interface may include the video showing the ultrasound imaging device and an arrow superimposed on the video that corresponds to the instruction.

24 Claims, 20 Drawing Sheets

(51) Int. Cl.
*G06F 3/0482* (2013.01)
*G06T 19/00* (2011.01)

(52) U.S. Cl.
CPC .............. *A61B 8/565* (2013.01); *A61B 8/582* (2013.01); *G06F 3/0482* (2013.01); *G06T 19/006* (2013.01)

(56) References Cited

U.S. PATENT DOCUMENTS

| | | | | |
|---|---|---|---|---|
| 8,069,420 | B2* | 11/2011 | Plummer | G16H 40/67 600/921 |
| 8,172,753 | B2 | 5/2012 | Halmann | |
| 8,253,779 | B2 | 8/2012 | Stetten | |
| 9,021,358 | B2 | 4/2015 | Amble et al. | |
| 2003/0191389 | A1* | 10/2003 | Sano | G16H 40/60 600/437 |
| 2004/0019270 | A1 | 1/2004 | Takeuchi | |
| 2005/0073575 | A1 | 4/2005 | Thacher et al. | |
| 2006/0074320 | A1* | 4/2006 | Yoo | A61B 8/08 600/472 |
| 2007/0242069 | A1 | 10/2007 | Matsue et al. | |
| 2008/0194960 | A1 | 8/2008 | Randall | |
| 2009/0189988 | A1* | 7/2009 | Jia | G05B 19/042 340/5.82 |
| 2011/0055447 | A1 | 3/2011 | Costa et al. | |
| 2013/0237811 | A1* | 9/2013 | Mihailescu | A61B 90/361 600/424 |
| 2013/0278635 | A1* | 10/2013 | Maggiore | G06F 3/0304 345/633 |
| 2014/0011173 | A1 | 1/2014 | Tepper et al. | |
| 2014/0243614 | A1 | 8/2014 | Rothberg et al. | |
| 2014/0282018 | A1* | 9/2014 | Amble | G16H 40/63 715/733 |
| 2015/0005630 | A1* | 1/2015 | Jung | A61B 8/465 600/437 |
| 2015/0035959 | A1* | 2/2015 | Amble | G16H 30/40 348/74 |
| 2017/0105701 | A1* | 4/2017 | Pelissier | G16H 30/40 |
| 2017/0360397 | A1 | 12/2017 | Rothberg et al. | |
| 2017/0360401 | A1* | 12/2017 | Rothberg | A61B 8/46 |
| 2017/0360402 | A1 | 12/2017 | de Jonge et al. | |
| 2017/0360403 | A1 | 12/2017 | Rothberg et al. | |
| 2017/0360404 | A1 | 12/2017 | Gafner et al. | |
| 2017/0360411 | A1 | 12/2017 | Rothberg et al. | |
| 2017/0360412 | A1 | 12/2017 | Rothberg et al. | |
| 2017/0367766 | A1* | 12/2017 | Mahfouz | A61B 8/56 |
| 2018/0110475 | A1* | 4/2018 | Shaya | G16H 10/20 |
| 2018/0279996 | A1* | 10/2018 | Cox | A61B 8/4254 |
| 2018/0295275 | A1* | 10/2018 | Azar | A61B 8/5207 |
| 2018/0344286 | A1* | 12/2018 | Mienkina | A61B 5/4848 |
| 2019/0038260 | A1* | 2/2019 | Lee | A61B 8/00 |
| 2019/0059851 | A1 | 2/2019 | Rothberg | |
| 2019/0117190 | A1* | 4/2019 | Djajadiningrat | G06T 19/006 |
| 2019/0239850 | A1* | 8/2019 | Dalvin | A61B 8/462 |
| 2019/0269386 | A1* | 9/2019 | Raju | A61B 8/0883 |
| 2020/0229798 | A1* | 7/2020 | Leyvi | A61B 8/4444 |

OTHER PUBLICATIONS

Suenaga et al., A Tele-Instruction System for Ulatrasound Probe Operation Based on Shared AR Technology. 23$^{rd}$ Annual International Conference of the IEEE Engineering in Medicine and Biology Society. Istanbul, Turkey. Oct. 25-28, 2001. 4 pages.

International Search Report and Written Opinion dated May 8, 2019 in connection with International Application No. PCT/US2019/019551.

Suenaga et al., A Tele-Instruction System for Ultrasound Probe Operation Based on Shared AR Technology. 2001 Proceedings of the 23$^{rd}$ Annual EMBS International Conference. Oct. 25, 2001; 3765-3768.

Extended European Search Report for European Application No. 19761665.9, dated Oct. 28, 2021.

\* cited by examiner

METHODS AND APPARATUS FOR TELE-MEDICINE

CROSS-REFERENCE TO RELATED APPLICATIONS

This application claims the benefit under 35 U.S.C. § 119(e) of U.S. Provisional Patent Application Ser. No. 62/636,127, filed Feb. 27, 2018 entitled "TELE-MEDICINE," which is hereby incorporated herein by reference in its entirety.

This application claims the benefit under 35 U.S.C. § 119(e) of U.S. Provisional Patent Application Ser. No. 62/646,333, filed Mar. 21, 2018 entitled "METHODS AND APPARATUS FOR TELE-MEDICINE," which is hereby incorporated herein by reference in its entirety.

FIELD

Generally, the aspects of the technology described herein relate to ultrasound data collection. Some aspects relate to ultrasound data collection using tele-medicine.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a probe), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an apparatus includes a user electronic device configured to receive an externally generated instruction for moving an ultrasound imaging device; and display, on a user augmented reality interface included on the user electronic device, the externally generated instruction for moving the ultrasound imaging device.

In some embodiments, the user electronic device is further configured to receive a video captured by a camera, the video depicting the ultrasound imaging device; and the user augmented reality interface includes the video depicting the ultrasound imaging device. In some embodiments, the user electronic device includes the camera. In some embodiments, the user electronic device is configured, when displaying the externally generated instruction on the user augmented reality interface, to display an arrow superimposed on the video showing the ultrasound imaging device. In some embodiments, the ultrasound imaging device includes one or more fiducial markers. In some embodiments, the user electronic device is further configured to determine a first transformation from a default pose of the camera relative to the one or more fiducial markers to a first pose of the camera relative to the one or more fiducial markers at a first time; and display the user augmented reality interface based on the first transformation. In some embodiments, the user electronic device is further configured to determine a second transformation from the default pose of the camera relative to the one or more fiducial markers to a second pose of the camera relative to the one or more fiducial markers at a second time after the first time, wherein the first transformation is different from the second transformation; and display the user augmented reality interface based on the second transformation. In some embodiments, the user electronic device is further configured to generate display the arrow in a direction that appears in the user augmented reality interface to be normal to one of the one or more fiducial markers. In some embodiments, the user electronic device is further configured to display the arrow such that the arrow appears in the user augmented reality interface to form a circular path parallel to a plane of one of the one or more fiducial markers. In some embodiments, the user electronic device is further configured to display the arrow such that the arrow appears in the user augmented reality interface to form a circular path orthogonal to a plane of one of the one or more fiducial markers. In some embodiments, the externally generated instruction is received from an instructor electronic device operated by an instructor.

In some embodiments, the user electronic device is further configured to receive an externally generated instruction to stop moving the ultrasound imaging device; and display, on the user electronic device, the externally generated instruction to stop moving the ultrasound imaging device. In some embodiments, the user electronic device is further configured to receive an externally generated instruction to stop moving the ultrasound imaging device; and cease to display, on the user augmented reality interface included on the user electronic device, the externally generated instruction for moving the ultrasound imaging device. In some embodiments, the user electronic device is further configured to receive an externally generated instruction to change an imaging preset; and change the imaging preset. In some embodiments, the user electronic device is further configured to receive an externally generated instruction to change an imaging gain; and change the imaging gain. In some embodiments, the user electronic device is further configured to receive an externally generated instruction to change the imaging depth; and change the imaging depth. In some embodiments, the user electronic device is further configured to receive an externally generated instruction to freeze an ultrasound image on a display screen of the user electronic device; and freeze the ultrasound image on the display screen on the user electronic device. In some embodiments, the user electronic device is further configured to receive an externally generated instruction to save one or more ultrasound images to memory; and save the one or more ultrasound images to memory. In some embodiments, the user electronic device is further configured to receive an externally generated instruction to move the ultrasound imaging device into a particular anatomical region; and display the externally generated instruction to move the ultrasound imaging device into the particular anatomical region. In some embodiments, the user electronic device is further configured to receive an externally generated instruction to instruct a subject to take and hold a deep breath; and display the externally generated instruction to instruct the subject to take and hold a deep breath.

In some embodiments, the user electronic device is further configured to receive an instruction to move the ultrasound imaging device into view of the camera; and display the instruction to move the ultrasound imaging device into view of the camera. In some embodiments, the user electronic device is further configured to receive an externally generated instruction to press the ultrasound imaging device harder onto a subject; and display the externally generated instruction to press the ultrasound imaging device harder onto the subject. In some embodiments, the user electronic device is further configured to receive an externally generated instruction to move the ultrasound imaging device in shorter and/or smaller increments; and display the externally generated instruction to move the ultrasound imaging device in shorter and/or smaller increments. In some embodiments, the user electronic device is further configured to transmit, to an instructor electronic device, ultrasound data collected by the ultrasound imaging device and/or an ultrasound image generated from the ultrasound data.

According to another aspect, an apparatus includes an instructor electronic device configured to display an instructor augmented reality interface depicting an ultrasound imaging device; receive, at the instructor augmented reality interface, an instruction for moving the ultrasound imaging device; and transmit, to a user electronic device, the instruction for moving the ultrasound imaging device.

In some embodiments, the instruction for moving the ultrasound imaging device is received from an instructor operating the instructor electronic device. In some embodiments, the instructor electronic device is further configured to receive a video captured by a camera, the video depicting the ultrasound imaging device; and the instructor augmented reality interface displays the video showing the ultrasound imaging device. In some embodiments, the instructor electronic device is further configured to display on the instructor augmented reality interface a superposition of a plurality of arrows on the video showing the ultrasound imaging device, wherein each of the plurality of arrows corresponds to a possible instruction for moving the ultrasound imaging device. In some embodiments, the instructor electronic device is further configured to receive a selection of one of the plurality of arrows on the instructor augmented reality interface, wherein the selected one of the plurality of arrows corresponds to the instruction for moving the ultrasound imaging device; and transmit the instruction to the user electronic device. In some embodiments, the instructor electronic device is further configured to receive a selection of an instruction to stop moving the ultrasound imaging device; and transmit, to the user electronic device, the instruction to stop moving the ultrasound imaging device. In some embodiments, the instructor electronic device is configured, when receiving the selection of one of the plurality arrows on the instructor augmented reality interface, to receive a continuous selection on the instructor augmented reality interface; and the instructor electronic device is further configured to receive, at the instructor electronic device, an instruction to stop moving the ultrasound imaging device, where receiving the instruction to stop moving the ultrasound imaging device includes detecting cessation of the continuous selection on the instructor augmented reality interface; and transmit, from the instructor electronic device to the user electronic device, the instruction to stop moving the ultrasound imaging device. In some embodiments, the instructor electronic device is configured, when receiving the continuous selection, to receive a continuous mouse click or receiving a continuous contact with touch-enabled sensors on a display screen. In some embodiments, the instructor electronic device is further configured to receive, on the instructor electronic device, a selection of an instruction to change an imaging preset; and transmit, from the instructor electronic device to the user electronic device, the instruction to change the imaging preset. In some embodiments, the instructor electronic device is further configured to receive a selection of an instruction to change an imaging gain; and transmit, to the user electronic device, the instruction to change the imaging gain. In some embodiments, the instructor electronic device is further configured to receive a selection of an instruction to change an imaging depth; and transmit, to the user electronic device, the instruction to change the imaging depth. In some embodiments, the instructor electronic device is further configured to receive a selection of an instruction to freeze an ultrasound image on a display screen of the user electronic device; and transmit, to the user electronic device, the instruction to freeze the ultrasound image on the display screen of the user electronic device. In some embodiments, the instructor electronic device is further configured to receive a selection of an instruction to save one or more ultrasound images to memory; and transmit, to the user electronic device, the instruction to save the one or more ultrasound images to memory. In some embodiments, the instructor electronic device is further configured to receive a selection of an instruction for the first user to move the ultrasound imaging device into a particular anatomical region; and transmit, to the user electronic device, the instruction for the first user to move the ultrasound imaging device into the particular anatomical region. In some embodiments, the instructor electronic device is further configured to receive a selection of an instruction for the first user to instruct a subject to take and hold a deep breath; and transmit, to the user electronic device, the instruction for the first user to instruct the subject to take and hold a deep breath. In some embodiments, the instructor electronic device is further configured to receive a selection of an instruction for the first user to move the ultrasound imaging device into view of the camera of the user electronic device; and transmit, to the user electronic device, the instruction for the first user to move the ultrasound imaging device into view of the camera of the user electronic device. In some embodiments, the instructor electronic device is further configured to receive a selection of an instruction for the first user to press the ultrasound imaging device harder onto a subject; and transmit, to the user electronic device, the instruction for the first user to press the ultrasound imaging device harder onto a subject. In some embodiments, the instructor electronic device is further configured to receive a selection of an instruction for the first user to move the ultrasound imaging device in shorter and/or smaller increments; and transmit, to the user electronic device, the instruction for the first user to move the ultrasound imaging device in shorter and/or smaller increments. In some embodiments, the instructor electronic device is further configured to receive, from the user electronic device, an ultrasound image; and display the ultrasound image.

Some aspects include at least one non-transitory computer-readable storage medium storing processor-executable instructions that, when executed by at least one processor, cause the at least one processor to perform the above functions. Some aspects include a method of performing the above functions.

According to another aspect, an apparatus includes an ultrasound imaging device and one or more fiducial markers coupled to the ultrasound imaging.

In some embodiments, the apparatus further includes a cube coupled to an end of the ultrasound imaging device, wherein the one or more fiducial markers are coupled to one or more surfaces of the cube. In some embodiments, the one or more fiducial markers include ArUco markers. In some embodiments, the cube includes two halves configured to couple together around the end of the ultrasound imaging device. In some embodiments, the apparatus further includes a cable, the cube includes a hole extending through the cube, and the cable extends from the end of the ultrasound imaging device through the cube.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
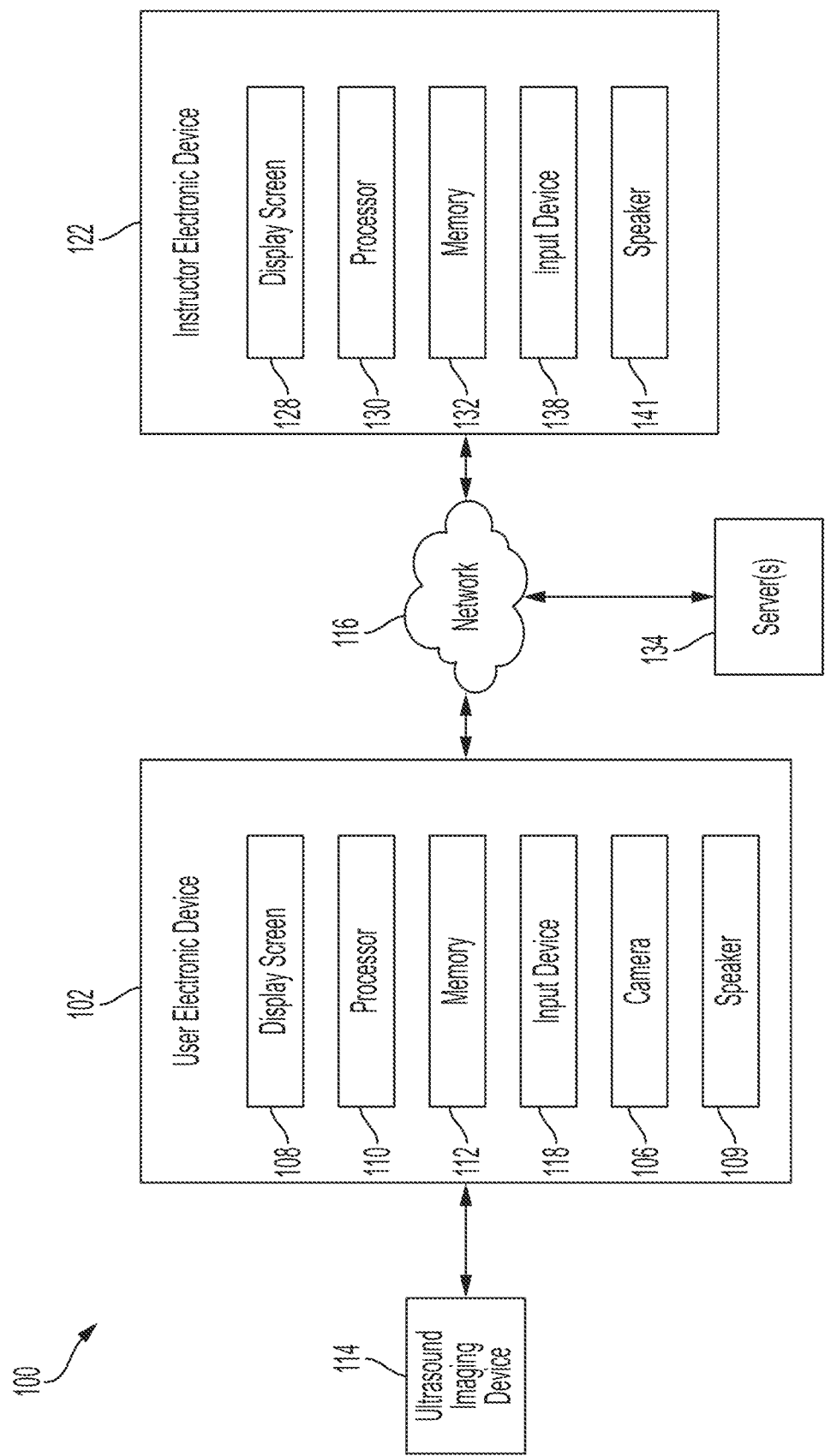
FIG. 1 illustrates a schematic block diagram of an example ultrasound system upon which various aspects of the technology described herein may be practiced.

Ultrasound examinations often include the acquisition of ultrasound images that contain a view of a particular anatomical structure (e.g., an organ) of a subject. Acquisition of these ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may make the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include: capturing ultrasound images of the incorrect anatomical structure, capturing foreshortened (or truncated) ultrasound images of the correct anatomical structure, and failing to perform a complete study of the relevant anatomy (e.g., failing to scan all the anatomical regions of a particular protocol).

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of ultrasound imaging devices makes them more accessible to the general populace, people who could make use of such devices have little to no training for how to use them. For example, a small clinic without a trained ultrasound technician on staff may purchase an ultrasound device to help diagnose patients. In this example, a nurse at the small clinic may be familiar with ultrasound technology and human physiology, but may know neither which anatomical views of a patient need to be imaged in order to identify medically-relevant information about the patient nor how to obtain such anatomical views using the ultrasound device. In another example, an ultrasound device may be issued to a patient by a physician for at-home use to monitor the patient's heart. In all likelihood, the patient understands neither human physiology nor how to image his or her own heart with the ultrasound device.

Accordingly, the inventors have developed tele-medicine technology, in which a human instructor, who may be remote from a user of an ultrasound imaging device, may instruct a user how to move the ultrasound imaging device in order to collect an ultrasound image. The inventors have recognized that instructing a user to move an ultrasound imaging device may involve the user needing to reconcile the pose of the ultrasound imaging device with the user's own pose. For example, consider a display showing an instruction constituting an image of an ultrasound imaging device and an arrow pointing away from a particular face of the ultrasound imaging device. In particular, consider that the particular face of the ultrasound imaging device is on the right side of the ultrasound imaging device as shown in the image, and the arrow is therefore pointing to the right. Depending on the pose of the user relative to the ultrasound imaging device, it is possible that the particular face of the ultrasound imaging device shown in the image may be on the user's left. Thus, the user may need to reconcile his or her own pose relative to the ultrasound imaging device and determine that following the instruction means moving the ultrasound imaging device to his or her left, despite the arrow in the instruction pointing to the right.

The inventors have recognized that it may be possible to automatically reconcile the pose of the ultrasound imaging device with the user's own pose using augmented reality (AR) interfaces. If the user is holding a user electronic device and viewing a user AR interface captured by the user electronic device's camera, then the pose of the user may be the same or similar to the pose of the camera. The user electronic device may automatically calculate transformations based on poses of the camera relative to the ultrasound imaging device as the camera moves. The user electronic device may then use this transformation to generate for display an arrow on the user AR interface that automatically maintains its direction relative to the ultrasound imaging device even as the camera and the user move. For example, consider the user AR interface showing an arrow pointing away from a particular face of the ultrasound imaging device, where the arrow points to the right in the user AR interface (from the perspective of the camera). Because the user AR interface shows the video captured by the camera, and because the camera's perspective is the same or similar to the user' perspective, then the particular face of the ultrasound imaging device may be on the user's right and the user may be able to follow this instruction by moving the ultrasound imaging device to his or her right, which is the same direction the arrow points in the user AR interface. If the user and the camera move such that the particular face of the ultrasound imaging device now faces the user's left, the user electronic device may calculate a transformation based on the newly captured video from the camera and use the transformation to change the arrow to point to the left on the user AR interface (from the perspective of the camera). The user may be able to follow the same instruction as before by moving the ultrasound imaging device to his or her left, which is the same direction the arrow points in the user AR interface. Because the user electronic device may automatically reconcile the user's pose with the pose of the ultrasound imaging device, the user may not need to perform this reconciliation himself or herself prior to following an instruction shown on the user AR interface.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

As referred to herein, an instruction to move an ultrasound imaging device should be understood to mean any indication of a movement of the ultrasound imaging device, with the intention that the movement of the ultrasound imaging device should occur. For example, an arrow pointing in a certain direction may be considered an instruction to move an ultrasound imaging device in that direction.

As referred to herein, receiving an instruction for moving an ultrasound imaging device should be understood to mean receiving any type of data containing/encoding an indication of an instruction to move the ultrasound imaging device.

As referred to herein, an externally generated instruction that is received at a first device should be understood to mean that an individual or a second device that is different than the first device generated the instruction.

As referred to herein, generating for display any indication of a movement of the ultrasound imaging device, with the intention that the movement of the ultrasound imaging device should occur. For example, generating for display an arrow pointing in a certain direction may be considered generating for display an instruction.

As referred to herein, an augmented reality (AR) interface should be understood to mean any interface superimposing non-real two-dimensional graphics on real-time images/video of the real three-dimensional world.

As referred to herein, an arrow should be understood to mean any graphic indicating a direction of movement, where the direction of movement may include a direction of translation, rotation, or tilting.

As referred to herein, a fiducial marker should be understood to mean any object in the field of view of an imager (e.g., a camera) which appears in an image/video produced by the imager for use as a point of reference or a measure. For example, an ArUco marker (i.e., a marker produced in accordance with the ArUco library for augmented reality applications) may be considered a fiducial marker.

As referred to herein, a pose should be understood to mean a position and/or orientation of one object relative to another object. For example, the position and/or orientation of a camera relative to a fiducial marker may be considered a pose of the camera relative to the fiducial marker.

As referred to herein, a transformation should be understood to mean any quantification of a change from one pose to another pose. For example, a transformation may be a transformation matrix describing translation, rotation, etc.

As referred to herein, generating an object for display based on a transformation should be understood to mean using the transformation when determining how to generate the object for display. For example, a transformation may describe a change in pose of a camera relative to a fiducial marker from a default pose to a current post. An electronic device may generate an arrow for display on an AR interface based on the transformation such that an arrow as seen from the perspective of the camera points in the same direction from the perspective of a fiducial marker despite changes in the pose of the camera relative to the fiducial marker.

FIG. 1 illustrates a schematic block diagram of an example ultrasound system 100 upon which various aspects of the technology described herein may be practiced. The ultrasound system 100 includes an ultrasound imaging device 114, a user electronic device 102, an instructor electronic device 122, and a network 116.

The user electronic device 102 includes a camera 106, a display screen 108, a processor 110, a memory 112, an input device 118, and a speaker 109. The instructor electronic device 122 includes a display screen 128, a processor 130, a memory 132, an input device 138, and a speaker 141. The user electronic device 102 is in wired (e.g., through a lightning connector or a mini-USB connector) and/or wireless communication (e.g., using BLUETOOTH, ZIGBEE, and/or WiFi wireless protocols) with the ultrasound imaging device 114. The user electronic device 102 is in wireless communication with the instructor electronic device 122 over the network 116. The user electronic device 102 and the instructor electronic device 122 12 are in wireless communication with one or more servers 134 over the network 116.

The ultrasound imaging device 114 may be configured to generate ultrasound data that may be employed to generate an ultrasound image. The ultrasound imaging device 114 may be constructed in any of a variety of ways. In some embodiments, the ultrasound imaging device 114 includes a transmitter that transmits a signal to a transmit beamformer which in turn drives transducer elements within a transducer array to emit pulsed ultrasonic signals into a structure, such as a patient. The pulsed ultrasonic signals may be backscattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound imaging device 114 may include one or more ultrasonic transducers monolithically integrated onto a single semiconductor die. The ultrasonic transducers may include, for example, one or more capacitive micromachined ultrasonic transducers (CMUTs), one or more piezoelectric micromachined ultrasonic transducers (PMUTs), and/or one or more other suitable ultrasonic transducer cells. In some embodiments, the ultrasonic transducers may be formed from or on the same chip as other electronic components (e.g., transmit circuitry, receive circuitry, control circuitry, power management circuitry, and processing circuitry) to form a monolithic ultrasound device.

Referring now to the user electronic device 102, the processor 110 may include specially-programmed and/or special-purpose hardware such as an application-specific integrated circuit (ASIC). For example, the processor 110 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The user electronic device 102 may be configured to process the ultrasound data from the ultrasound imaging device 114 received from the ultrasound imaging device 114 to generate ultrasound images for display on the display screen 108. The processing may be performed by, for example, the processor 110. The processor 110 may also be adapted to control the acquisition of ultrasound data with the ultrasound imaging device 114. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The user electronic device 102 may be configured to perform certain of the processes described herein using the processor 110 (e.g., one or more computer hardware processors) and one or more articles of manufacture that include non-transitory computer-readable storage media such as the memory 112. The processor 110 may control writing data to and reading data from the memory 112 in any suitable manner. To perform certain of the processes described herein, the processor 110 may execute one or more processor-executable instructions stored in one or more non-transitory computer-readable storage media (e.g., the memory 112), which may serve as non-transitory computer-readable storage media storing processor-executable instructions for execution by the processor 110. The camera 106 may be configured to detect light (e.g., visible light) to form an image. The display screen 108 may be configured to display images and/or videos, and may be, for example, a liquid crystal display (LCD), a plasma display, and/or an organic light emitting diode (OLED) display on the user electronic device 102. The input device 118 may include one or more devices capable of receiving input from a user and transmitting the input to the processor 110. For example, the input device 118 may include a keyboard, a mouse, a microphone, and/or touch-enabled sensors on the display screen 108. The speaker 109 may be configured to output audio. The display screen 108, the input device 118, the camera 106, and the speaker 109 may be communicatively coupled to the processor 110 and/or under the control of the processor 110.

It should be appreciated that the user electronic device 102 may be implemented in any of a variety of ways. For example, the user electronic device 102 may be implemented as a handheld device such as a mobile smartphone or a tablet. Thereby, a user of the ultrasound imaging device 114 may be able to operate the ultrasound imaging device 114 with one hand and hold the user electronic device 102 with another hand. In other examples, the user electronic device 102 may be implemented as a portable device that is not a handheld device, such as a laptop. In yet other examples, the user electronic device 102 may be implemented as a stationary device such as a desktop computer. The user electronic device 102 may be connected to the network 116 over a wired connection (e.g., via an Ethernet cable) and/or a wireless connection (e.g., over a WiFi network). The user electronic device 102 may thereby communicate with the instructor electronic device 122 and/or to the servers 134 over the network 116.

Referring now to the instructor electronic device 122, the processor 130 may include specially-programmed and/or special-purpose hardware such as an application-specific integrated circuit (ASIC). For example, the processor 130 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The instructor electronic device 122 may be configured to perform certain of the processes described herein using the processor 130 (e.g., one or more computer hardware processors) and one or more articles of manufacture that include non-transitory computer-readable storage media such as the memory 132. The processor 130 may control writing data to and reading data from the memory 132 in any suitable manner. To perform certain of the processes described herein, the processor 130 may execute one or more processor-executable instructions stored in one or more non-transitory computer-readable storage media (e.g., the memory 132), which may serve as non-transitory computer-readable storage media storing processor-executable instructions for execution by the processor 130. The display screen 128 may be configured to display images and/or videos such as a liquid crystal display (LCD), a plasma display, and/or an organic light emitting diode (OLED) display on the user electronic device 102. The input device 138 may include one or more devices capable of receiving input from a user and transmitting the input to the processor 130. For example, the input device 138 may include a keyboard, a mouse, a 3D mouse (e.g., a SpaceMouse®), a microphone, a controller using gesture recognition (e.g., a Leap Motion® controller) and/or touch-enabled sensors on the display screen 128. The speaker 14 may be configured to output audio. The display screen 128, the input device 138, and the speaker 141 may be communicatively coupled to the processor 130 and/or under the control of the processor 130.

It should be appreciated that the instructor electronic device 122 may be implemented in any of a variety of ways. For example, the instructor electronic device 122 may be implemented as a handheld device such as a mobile smartphone or a tablet, as a portable device that is not a handheld device such as a laptop, or a stationary device such as a desktop computer. The instructor electronic device 122 may be connected to the network 136 over a wired connection (e.g., via an Ethernet cable) and/or a wireless connection (e.g., over a WiFi network). The instructor electronic device 122 may thereby communicate with the user electronic device 102 and/or to the servers 134 over the network 116.

As will be discussed further below, the user electronic device 102 and the instructor electronic device 122 may communicate video, audio, and other forms of data (e.g., instructions for moving the ultrasound imaging device 114). This communication may occur over the network 116 using a peer-to-peer network link. For further discussion of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application).

FIG. 1 should be understood to be non-limiting. For example, the ultrasound system 100 may include fewer or more components than shown, the user electronic device 102 may include fewer or more components than shown, and the instructor electronic device 122 may include fewer or more components than shown.

Figure 2:
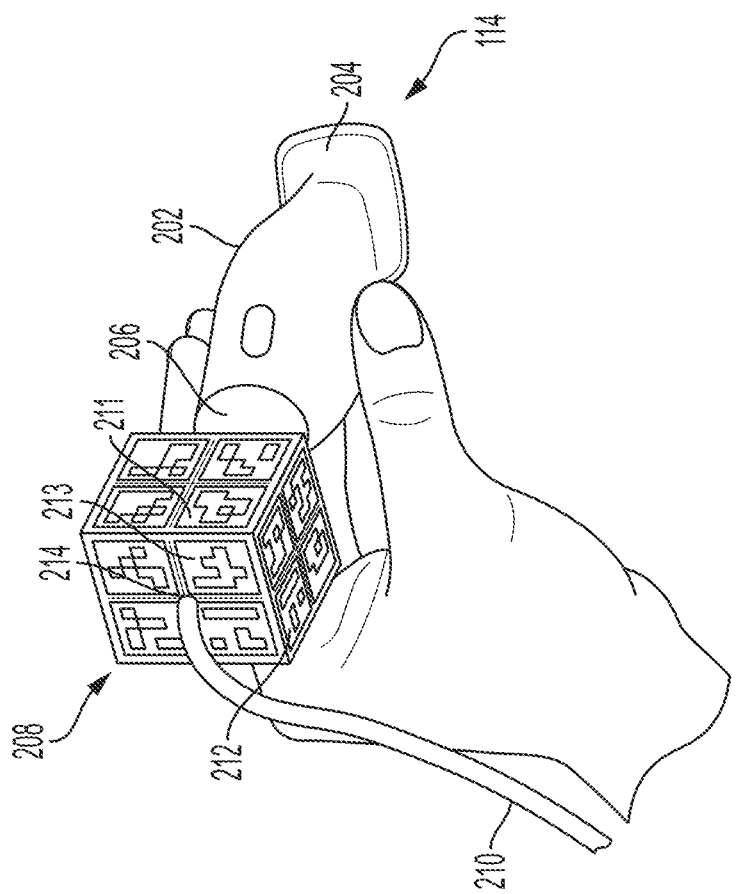
FIG. 2 shows an example of an ultrasound imaging device that may be used in conjunction with certain embodiments described herein.

FIG. 2 shows an example of the ultrasound imaging device 114 that may be used in conjunction with certain embodiments described herein. The ultrasound imaging device 114 includes a body 202 having a first end 204 and a second end 206, a fiducial marker cube 208, and a cable 210. An ultrasound sensor head (not visible in FIG. 2) is disposed at the first end 204. The fiducial marker cube 208 is coupled to the second end 206 of the body 202. The fiducial marker cube 208 includes a plurality of fiducial markers disposed on the five surfaces of the fiducial marker cube 208 that do not face the second end 206 of the body 202. In FIG. 2, fiducial markers 211-213 are visible. In FIG. 2, the fiducial markers are ArUco markers, but other markers may be used (e.g., holographic markers, dispersive markers). The face of the fiducial marker cube 208 facing away from the second end 206 of the body 202 includes a hole 214. The cable 210 extends from the second end 206 of the body 202 through the hole 214. The cable 210 may transmit electrical signals from the ultrasound imaging device 114 to an external processing device, such as the user electronic device 102. In some embodiments, the ultrasound imaging device 114 may transmit electrical signals (e.g., to the user electronic device 102) wirelessly, and the cable 210 and the hole 214 may be absent.

Figure 3:
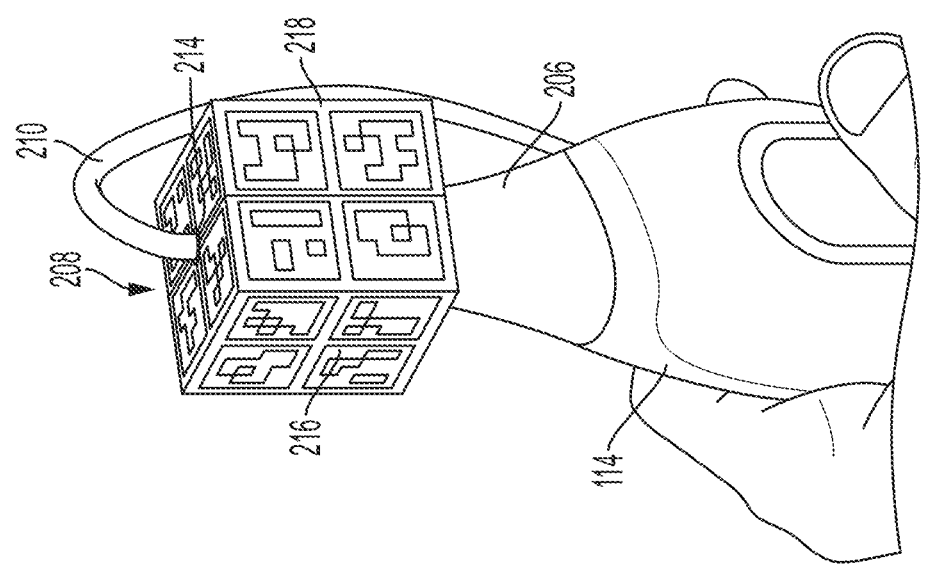
FIGS. 3-4 show an embodiment of the ultrasound imaging device of FIG. 2, in which the ultrasound imaging device includes a fiducial marker cube having two halves.
Figure 4:
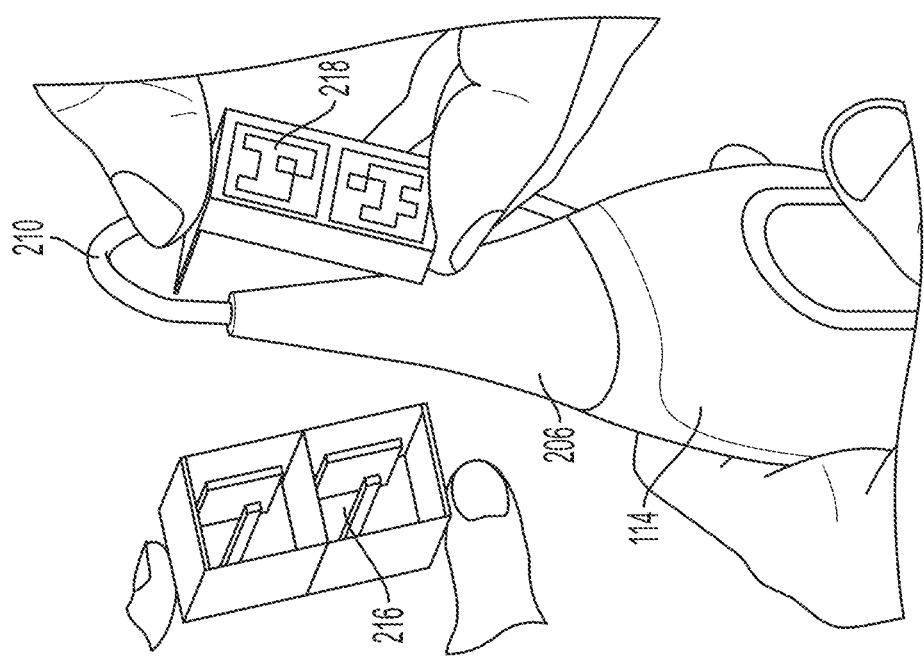

FIGS. 3-4 show an embodiment of the ultrasound imaging device 114 in which the fiducial marker cube 208 has two halves 216 and 218. The two halves 216 and 218 of the fiducial marker cube 208 couple together around the second end 206 of the body 202 and the cable 210. Half of the hole 214 is formed in the half 216 and half of the hole 214 is formed in the half 218. FIG. 3 shows the two halves 216 and 218 of the fiducial marker cube 208 coupled together around the second end 206 of the body 202. FIG. 4 shows the two halves 216 and 218 of the fiducial marker cube 208 split from each other and removed from the second end 206 of the body 202. Splitting the fiducial marker cube 208 into the two halves 216 and 218 may constitute an easy way to remove the fiducial marker cube 208 from the ultrasound imaging device 114.

Figure 5:
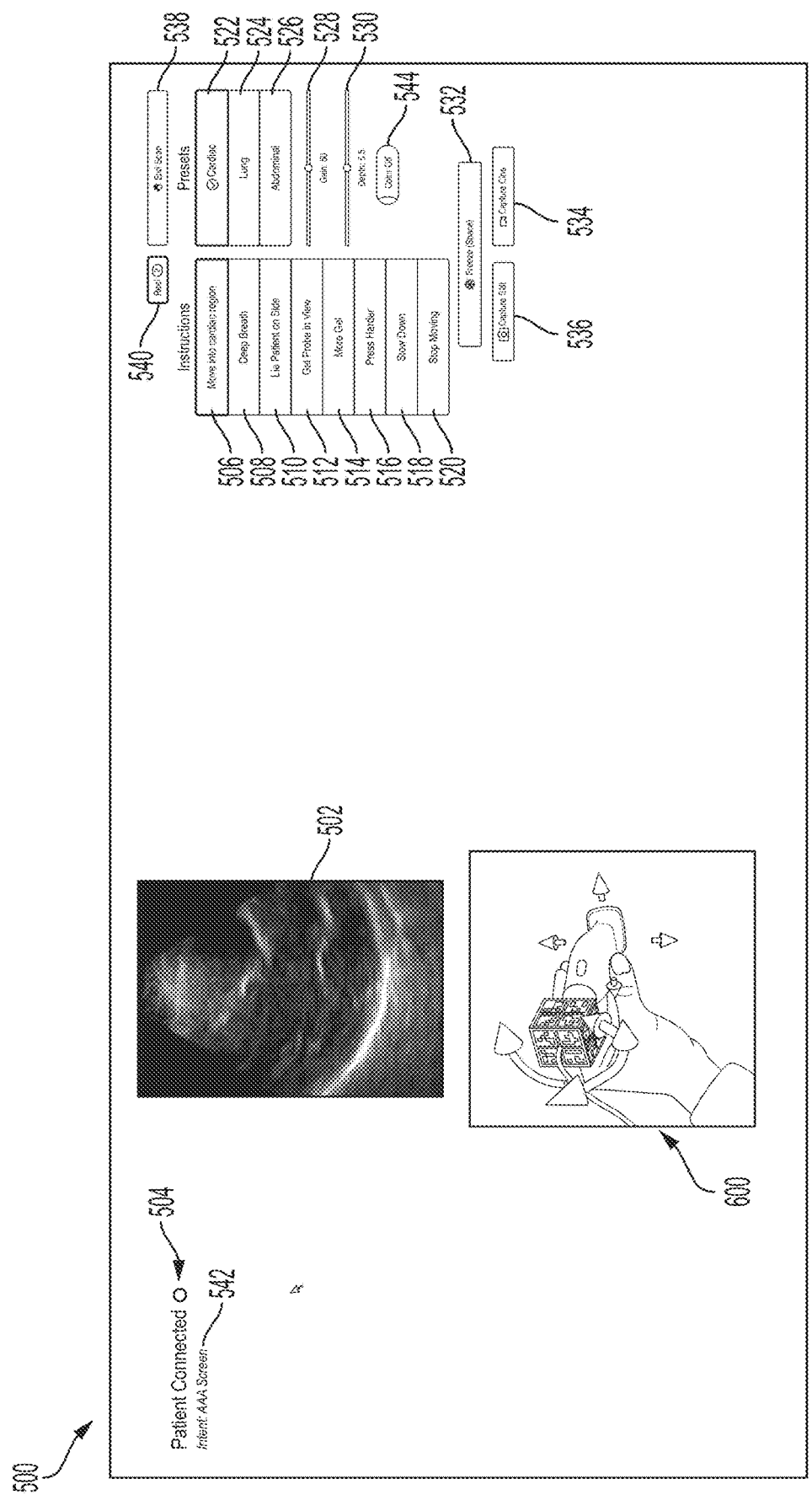
FIG. 5 shows an example instructor interface that may be generated for display on an instructor electronic device, where the instructor interface includes an instructor AR interface showing multiple arrows.

FIG. 5 shows an example instructor interface 500 that may be generated for display by the instructor electronic device 122. For example, the instructor electronic device 122 may generate for display the instructor interface 500 on the display screen 128 of the instructor electronic device 122. The instructor interface 500 includes an instructor augmented reality (AR) interface 600, an ultrasound image 502, a patient connection indicator 504, an intent indicator 542, and a menu of instructions (options) the instructor may select including, but not necessarily limited to: an option 506 to instruct the user to move the ultrasound imaging device 114 into a particular anatomical region on the subject, an option 508 to instruct the user to instruct the subject to take and hold a deep breath, an option 510 to instruct the user to instruct the subject to lie on his or her side, an option 512 to instruct the user to move the ultrasound imaging device 114 into the view of the camera 106, an option 514 to instruct the user to apply more gel to the subject, an option 516 to instruct the user to press the ultrasound imaging device 114 harder onto the subject, an option 518 to instruct the user to move the ultrasound imaging device 114 in smaller and/or shorter increments, an option 520 to instruct the user to stop moving the ultrasound imaging device 114, a cardiac preset option 522, a lung preset option 524, an abdominal preset option 526, a gain slider 528, a depth slider 530, a color option 544, a freeze option 532, a still capture option 536, a cine capture option 534, an end scan option 538, and a reel indicator 540. As will be discussed further, the instructor AR interface 600 may include images/video of the real three-dimensional world with non-real two-dimensional graphics superimposed on the images/video of the real three-dimensional world such, and thus be considered an AR interface. FIG. 5 should be understood to be non-limiting. For example, the instructor interface 500 may include fewer or more components than shown, and/or the components of the instructor interface 500 may be arranged differently or have different forms than shown.

Figure 6:
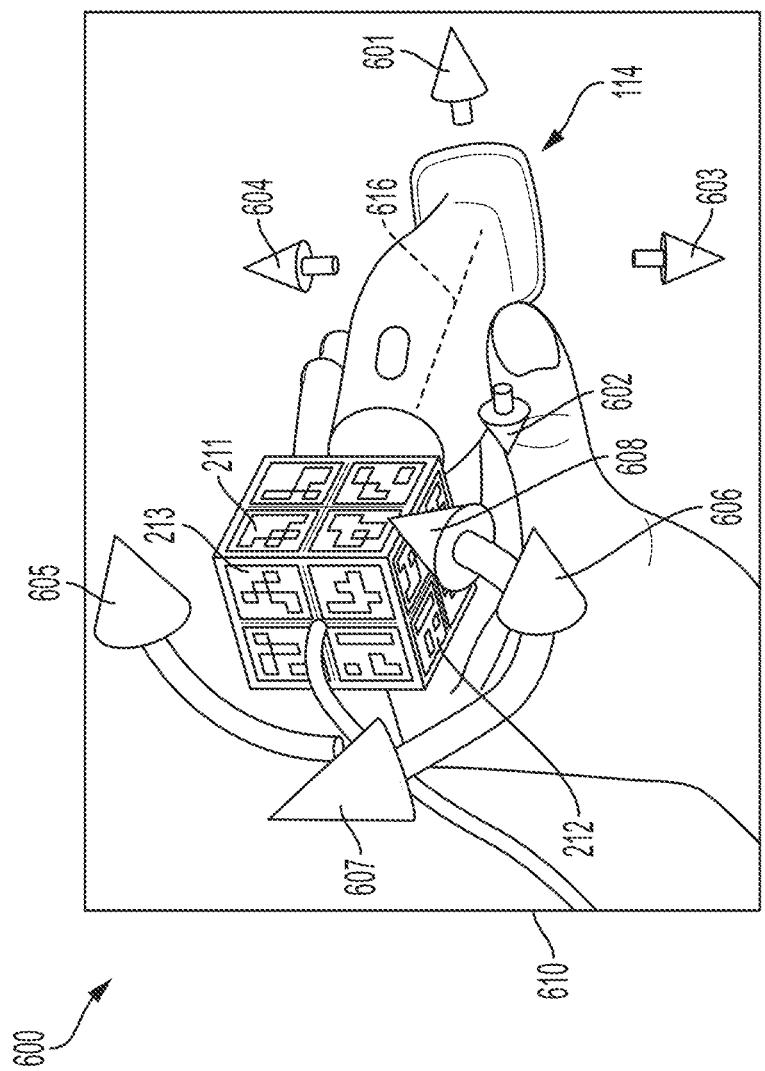
FIG. 6 illustrates the instructor augmented reality (AR) interface in detail, where the instructor AR interface shows a video image captured by a camera.

FIG. 6 illustrates the instructor AR interface 600 as shown in FIG. 5 in more detail. The instructor AR interface 600 includes a frame of a video 610 of the ultrasound imaging device 114 and arrows 601-608 superimposed on the frame of the video 610. In some embodiments, the camera 106 of the user electronic device may capture a frame of the video 610, transmit the frame of the video 610 to the instructor electronic device 122, and the instructor electronic device 122 may generate the frame of the video 610 for display on the instructor interface 500. When a new frame of the video 610 is collected, the user electronic device 102 may transmit (e.g., over a wireless connection) the new frame of the video 610 to the instructor electronic device 122, which may update the frame of the video 610 shown on the instructor interface 500 with the new frame of the video 610. The user of the ultrasound imaging device 114 may hold the ultrasound imaging device 114 on the subject being imaged and position the camera 106 of the user electronic device 102 (which the user may also be holding) such that the ultrasound imaging device 114 is in view of the camera 106.

The arrows 601-608 are shown superimposed on the video of the ultrasound imaging device 114 and may correspond to possible instructions for moving the ultrasound imaging device 114, namely instructions to translate, rotate, and/or tilt the ultrasound imaging device 114. Instructions for moving the ultrasound imaging device 114 may include any combination of instructions to translate the ultrasound imaging device 114, instructions to rotate the ultrasound imaging device 114 (i.e., rotation about the longitudinal axis of the ultrasound imaging device 114), and instructions to tilt the ultrasound imaging device 114 (e.g., tilting the ultrasound imaging device 114 about the end portion of the ultrasound imaging device 114 contacting the subject). The instructions to move the ultrasound imaging device 114 may be instructions designed to move the ultrasound imaging device 114 from a current position to a position and orientation on a subject such that a target anatomical view (e.g., a parasternal long axis view of the heart) can be obtained. As will be discussed further below, the instructor may select one of the possible instructions for moving the ultrasound imaging device 114, and the instructor electronic device 122 may transmit this instruction to the user electronic device 102 and thereby instruct the user to move the ultrasound imaging device 114 in accordance with the selected instruction.

The arrow 601 as displayed in the instructor AR interface 600 is normal to the fiducial marker 211 and faces the direction which the fiducial marker 211 faces. Generating the arrow 601 for display may be helpful as an instruction for translating the ultrasound imaging device 114 in the direction which the fiducial marker 211 faces. The arrow 602 as displayed in the instructor AR interface 600 is normal to the fiducial marker 211 and faces opposite the direction which the fiducial marker 211 faces. Generating the arrow 602 for display may be helpful as an instruction for translating the ultrasound imaging device 114 opposite the direction which the fiducial marker 211 faces. The arrow 603 as displayed in the instructor AR interface 600 is normal to the fiducial marker 212 and faces the direction which the fiducial marker 212 faces. Generating the arrow 603 for display may be helpful as an instruction for translating the ultrasound imaging device 114 in the direction which the fiducial marker 212 faces. The arrow 604 as displayed in the instructor AR interface 600 is normal to the fiducial marker 212 and faces opposite the direction which the fiducial marker 212 faces. Generating the arrow 604 for display may be helpful as an instruction for translating the ultrasound imaging device 114 opposite the direction which the fiducial marker 212 faces. The fiducial marker 213 lies in a plane orthogonal to the longitudinal axis 616 of the ultrasound imaging device 114. The arrow 605 as displayed in the instructor AR interface 600 forms a circular path parallel to the plane of the fiducial marker 212. Generating the arrow 605 for display may be helpful as an instruction for rotating the ultrasound imaging device 114 in the direction indicated by the arrow 605. The arrow 606 as displayed in the instructor AR interface 600 forms a circular path parallel to the plane of the fiducial marker 212 that is opposite in direction as the path of the arrow 605. Generating the arrow 606 for display may be helpful as an instruction for rotating the ultrasound imaging device 114 in the direction indicated by the arrow 606. The arrow 607 as displayed in the instructor AR interface 600 forms a circular path orthogonal to the plane of the fiducial marker 212. Generating the arrow 607 for display may be helpful as an instruction for tilting the ultrasound imaging device 114 in the direction indicated by the arrow 607. The arrow 608 as displayed in the instructor AR interface 600 forms a circular path orthogonal to the plane of the fiducial marker 212 that is opposite in direction as the path of the arrow 607. Generating the arrow 608 for display may be helpful as an instruction for tilting the ultrasound imaging device 114 in the direction indicated by the arrow 608. It should be noted that two additional arrows, corresponding to the other two directions for tilting the ultrasound imaging device 114 that are not indicated by the arrow 607 and the arrow 608, may also be displayed on the AR interface 600.

The instructor electronic device 122 may receive, from the user electronic device 102, a transformation based on a pose of the camera 106 of the user electronic device 102. The transformation may describe a change in pose of the camera 106 from (1) a default pose of the camera 106 relative to the fiducial markers on the ultrasound imaging device 114 to (2) the current pose of the camera 106 relative to the fiducial markers on the ultrasound imaging device 114 when the camera captured the frame of the video 610. The transformation may include a quantification of translations, rotations, and/or tilts of the camera 106 from the default pose to the current pose, and may be in the form of a matrix. The user electronic device 102 may use pose estimation techniques to analyze the particular frame of the video 610 to determine the transformation at the particular time when the frame of the video 610 was captured. In embodiments in which the instructor electronic device 122 continuously receives video, the instructor electronic device 122 may continuously receive updated transformations based on the current frame of the video 610 throughout the imaging session.

In the embodiment of FIG. 6, the ultrasound imaging device 114 includes fiducial markers coupled to the ultrasound imaging device 114. Therefore, the transformation describing changes in the pose of the camera 106 relative to the fiducial markers may equivalently describe changes in the pose of the camera 106 relative to the ultrasound imaging device 114. (As referred to herein, if fiducial markers are coupled to an ultrasound imaging device 114, references to the pose of the camera 106 relative to the ultrasound imaging device 114 should be understood to be interchangeable with references to the pose of the camera 106 relative to the fiducial markers.) If the camera 106 moves relative to the ultrasound imaging device 114, the transformation may capture that movement. In particular, the transformation may describe how to change the direction of an arrow (e.g., one of the arrows 601-608) relative to the camera 106 such that the direction of the arrow relative to the ultrasound imaging device 114 as seen in the instructor AR interface 600 remains constant even if the camera 106 moves relative to the ultrasound imaging device 114.

Figure 7:
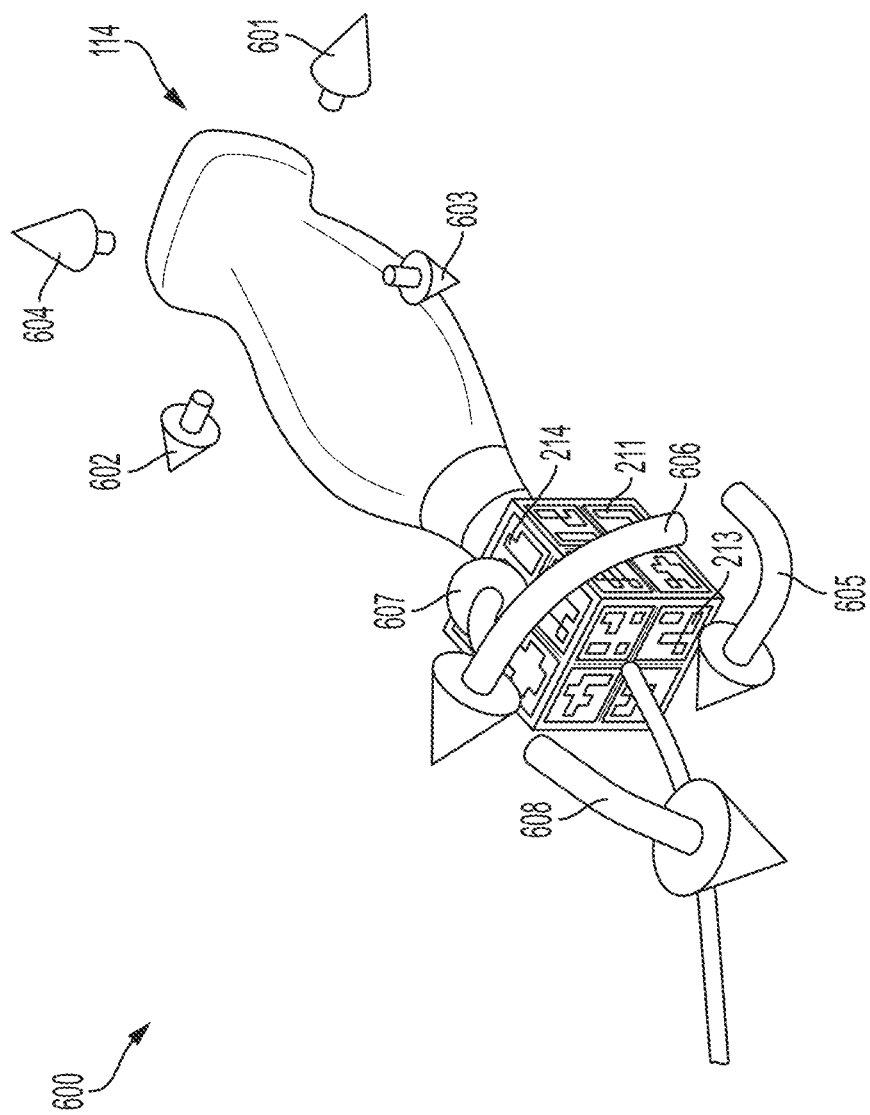
FIG. 7 shows the instructor AR interface of FIG. 6, where the instructor AR interface shows a video image captured by the camera while at a different pose relative to the ultrasound imaging device.

As an illustration of the above discussion, FIG. 7 shows the instructor AR interface 600, but the pose of the camera 106 relative to the ultrasound imaging device 114 has changed from the pose in FIG. 6. The arrows 601-608 from the perspective of the camera point in different directions in FIG. 7 than they do in FIG. 6. For example, the arrow 601 in FIG. 6 points substantially rightwards and upwards from the perspective of the camera 106 while the arrow 601 in FIG. 7 points substantially rightwards and downwards from the perspective of the camera 106. Nevertheless, the arrows 601-608 still point in the same directions relative to the ultrasound imaging device 114 as in FIG. 6. For example, the arrow 601 points away from the same face of the ultrasound imaging device 114 in both FIGS. 6 and 7. The transformation used by the instructor electronic device 122 for generating the instructor AR interface 600 for display may describe how to generate for display the arrows 601-

608 from the perspective of the camera 106 such that they point in the same directions from the perspective of the ultrasound imaging device 114 despite changes in the pose of the camera 106 relative to the ultrasound imaging device 114. (It should be noted that in FIG. 7, the fiducial marker 212 is not visible, while a fiducial marker 214 opposite the fiducial marker 212 is now visible.)

As discussed above, the user electronic device 102 may be in communication with the ultrasound imaging device 114. In some embodiments, the ultrasound imaging device 114 may collect ultrasound data, transmit the ultrasound data to the user electronic device 102, and the user electronic device 102 may generate the ultrasound image 502 from the ultrasound data. In some embodiments, the ultrasound imaging device 114 may collect ultrasound data, generate the ultrasound image 502 from the ultrasound data, and transmit the ultrasound image 502 to the user electronic device 102. The user electronic device 102 may transmit the ultrasound image 502 to the instructor electronic device 122, and the instructor electronic device 122 may generate the ultrasound image 502 for display on the instructor interface 500. When new ultrasound data is collected and a new ultrasound image is generated, the user electronic device 102 may transmit the new ultrasound image 502 to the instructor electronic device 122, and the instructor electronic device 122 may update the ultrasound image 502 shown on the instructor interface 500 with the new ultrasound image 502.

Figure 8:
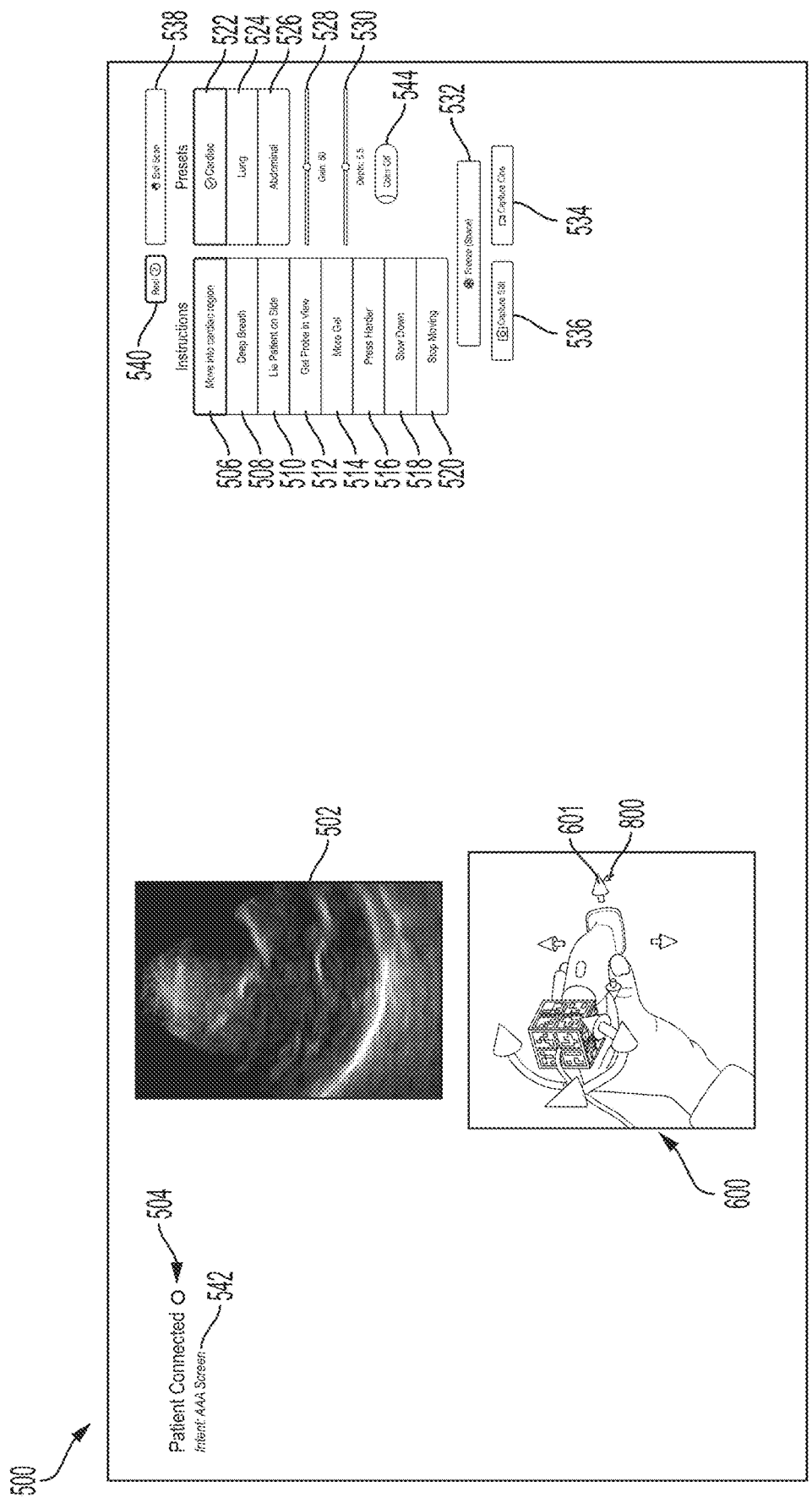
FIG. 8 illustrates the instructor interface of FIG. 5 receiving, from an instructor, a selection of one of the arrows shown on the instructor AR interface.

FIG. 8 illustrates the instructor interface 500 receiving a selection of an arrow from an instructor. The instructor interface 500 may receive the selection of the arrow using the input device 138 of the instructor electronic device. In the example of FIG. 8, the input device 138 includes a mouse, and a mouse cursor 800 hovers over a particular arrow 601 in the user AR interface 600. Once the mouse is clicked by the instructor, the arrow 601 is selected. In other embodiments, the input device 138 may include touch-enabled sensors on the display screen 128 of the instructor electronic device 122, and the instructor may touch the arrow 601 on the display screen 128 to select the arrow 601. The instructor may use the ultrasound image 502 and/or the frame of the video 610 of the ultrasound imaging device 114 to decide how to instruct the user to move the ultrasound imaging device 114.

Figure 9:
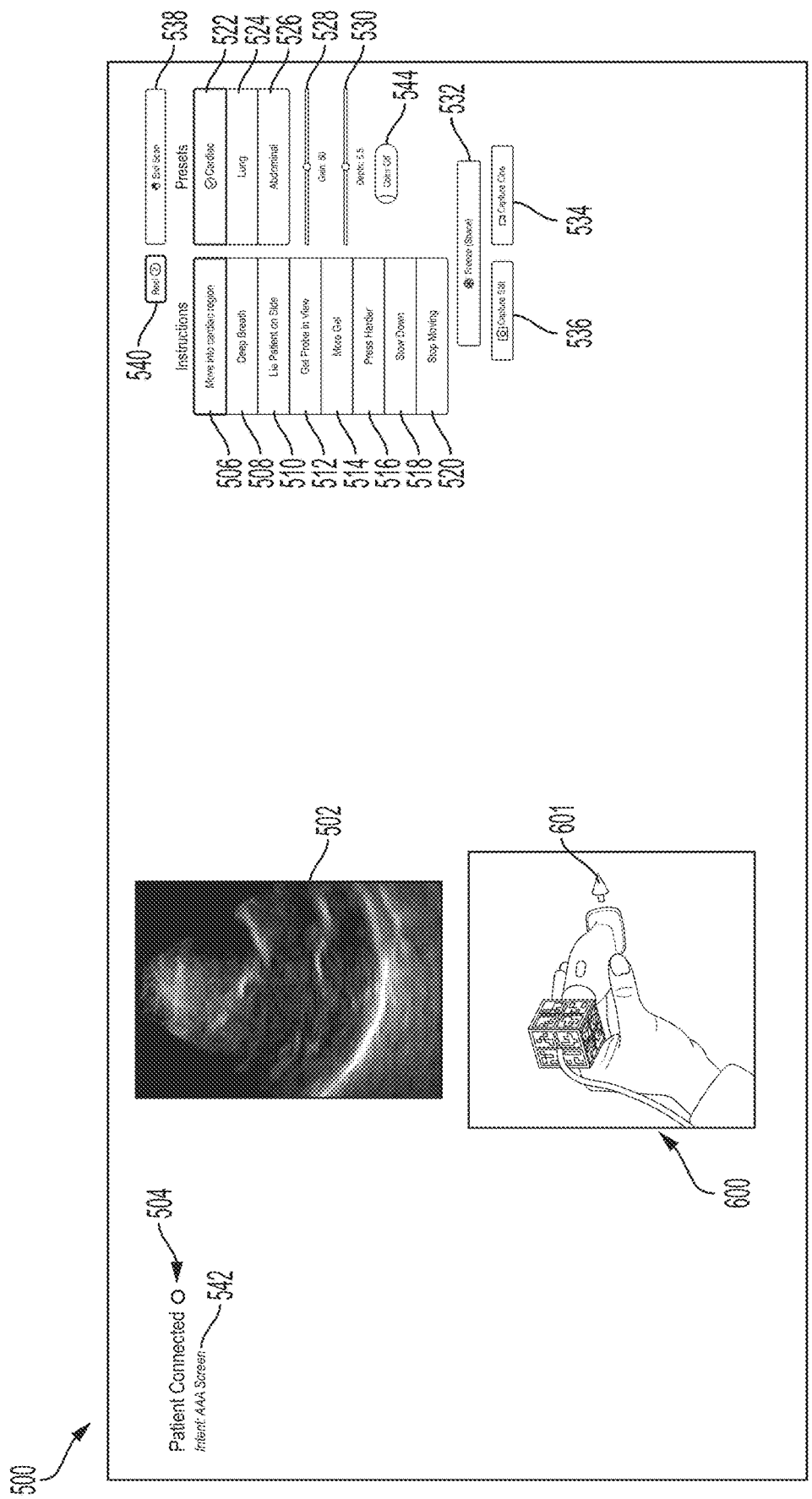
FIG. 9 illustrates the instructor interface of FIG. 5 after receiving the selection of the arrow.

FIG. 9 illustrates the instructor interface 500 after receiving the selection of the arrow from the instructor. On the instructor AR interface 600, only the selected arrow 601 is shown, while other arrows previously shown on the instructor AR interface 600 are not shown. After receiving the selection of the arrow 601, which corresponds to an instruction for moving the ultrasound imaging device 114, the instructor electronic device 122 may transmit the instruction to the user electronic device 102. In some embodiments, each of the arrows 601-608 shown in the instructor AR interface 600 may have an identifier, and the instructor electronic device 122 may transmit the identifier of the selected arrow 601 to the user electronic device 102. For example, consider the arrow 601 selected in FIG. 8. The arrow 601 may point to the right in a default pose of the camera 106 relative to the ultrasound imaging device 114. As discussed above, as the pose of the camera 106 relative to the ultrasound imaging device 114 changes, the direction of the arrow 601 from the perspective of the camera 106 may change such that the direction of the arrow 601 from the perspective of the ultrasound imaging device 114 remains substantially constant. At any given time, however, the arrow 601 may be identified as the "right" arrow, based on its direction from the perspective of the camera 106 in the default pose, despite the arrow 601 not necessarily pointing to the right from the perspective of the camera 106 at the given time. If the arrow 601 identified as "right" is selected in FIG. 8, the instructor electronic device 122 may transmit the instruction corresponding to this arrow 601 by transmitting the identifier "right." In some embodiments, each of the arrows 601-608 may have other types of identifiers, such as alphanumeric identifiers without descriptive meaning.

Figure 10:
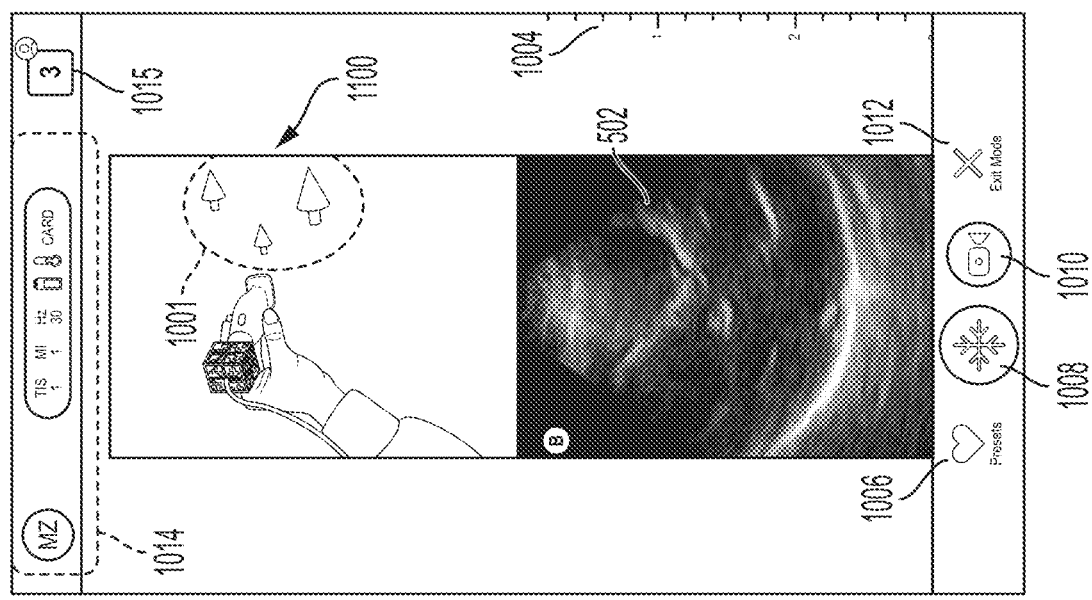
FIG. 10 illustrates an example user interface that may be generated for display on a user electronic device, where the user interface includes a user AR interface.

FIG. 10 illustrates an example user interface 1000 generated for display by the user electronic device 102. For example, the user electronic device 102 may generate for display the user interface 1000 on the display screen 108 of the user electronic device 102. The user interface 1000 includes an user AR interface 1100, the ultrasound image 502, a depth scale 1004, a preset menu option 1006, a still capture option 1008, a cine capture option 1010, an exit mode option 1012, an information panel 1014, and a real indicator 1015. FIG. 10 should be understood to be non-limiting. For example, the user interface 1000 may include fewer or more components than shown, and/or the components of the user interface 1000 may be arranged differently or have different forms than shown.

As discussed above, the user electronic device 102 may be in communication with the ultrasound imaging device 114. In some embodiments, the ultrasound imaging device 114 may collect ultrasound data, transmit the ultrasound data to the user electronic device 102, and the user electronic device 102 may generate the ultrasound image 502 from the ultrasound data. In some embodiments, the ultrasound imaging device 114 may collect ultrasound data, generate the ultrasound image 502 from the ultrasound data, and transmit the ultrasound image 502 to the user electronic device 102. The user electronic device 102 may generate the ultrasound image 502 for display on the user interface 1000, as shown in FIG. 10. The user electronic device 102 may also transmit the ultrasound image 502 to the instructor electronic device 122, which may generate the ultrasound image 502 for display on the instructor interface 500, as shown, for example, in FIG. 5. When new ultrasound data is collected and a new ultrasound image is generated, the user electronic device 102 may update the ultrasound image 502 shown on the user interface 1000 with the new ultrasound image 502. The user electronic device 102 may also transmit the new ultrasound image 502 to the instructor electronic device 122, which may update the ultrasound image 502 shown on the instructor interface 500 with the new ultrasound image 502. Accordingly, at any given time, the user interface 1000 and the instructor interface 500 may show the same ultrasound image 502, which may be generated from the most recent ultrasound data collected by the ultrasound imaging device 114. (However, there may be a lag time between when the user electronic device 102 generates the ultrasound image 502 for display and when the instructor electronic device 122 generates the ultrasound image 502 for display due to the time required to transmit the ultrasound image 502 from the user electronic device 102 to the instructor electronic device 122.) The instructor may use the ultrasound image 502 as shown on the instructor interface 500 to decide how to instruct the user to move the ultrasound imaging device 114.

In some embodiments, the camera 106 of the user electronic device may capture a frame of the video 610 and generate the frame of the video 610 for display on the user interface 1000, as shown in FIG. 10. The user electronic device 102 may also transmit the frame of the video 610 to the instructor electronic device 122, which may generate the frame of the video 610 for display on the instructor interface 500, as shown, for example, in FIG. 5. When a new frame of the video 610 is collected, the user electronic device 102 may update the frame of the video 610 shown on the user interface 1000 with the new frame of the video 610. The user electronic device 102 may also transmit the new frame of the video 610 to the instructor electronic device 122, which may update the frame of the video 610 shown on the instructor interface 500 with the new frame of the video 610. Accordingly, at any given time, the user interface 1000 and the instructor interface 500 may show the same frame of the video 610. (However, there may be a lag time between when the user electronic device 102 generates the frame of the video 610 for display and when the instructor electronic device 122 generates the frame of the video 610 for display due to the time required to transmit the frame of the video 610 from the user electronic device 102 to the instructor electronic device 122.)

Figure 11:
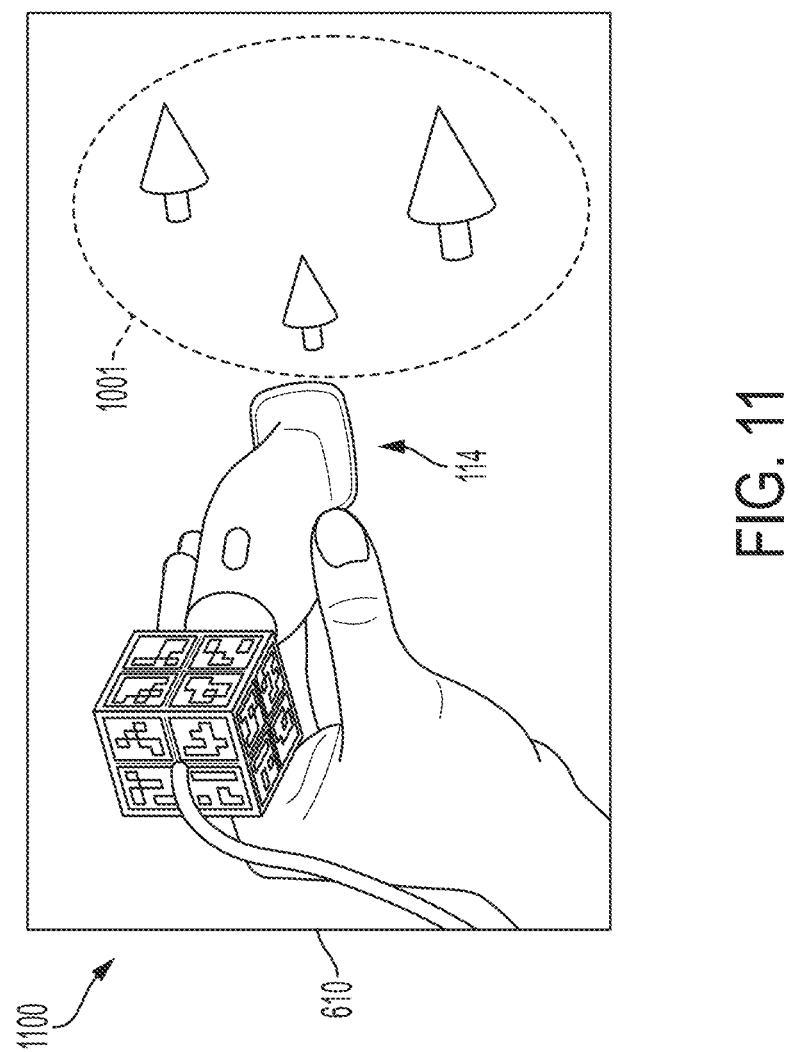
FIG. 11 illustrates a user AR interface in detail.

FIG. 11 illustrates the user AR interface 1100 in more detail. The user AR interface 1100 includes a frame of the video 610 of the ultrasound imaging device 114 (captured by the camera 106 of the user electronic device 102 and transmitted to the instructor electronic device 122 for display on the instruct AR interface 500). The user AR interface 1100 further shows arrows 1001. As discussed above, the instructor electronic device 122 may receive a selection of an arrow from among a plurality of arrows on the instructor interface 500. In the example of FIG. 8, the arrow 601 has been selected. After receiving the selection of the arrow 601, which corresponds to an instruction for moving the ultrasound imaging device 114, the instructor electronic device 122 may transmit the instruction to the user electronic device 102, which may receive the instruction and generate the arrows 1001 for display on the user AR interface 1100. As discussed above, in some embodiments, the instruction received by the user electronic device 102 may include an identifier of the arrow 601 selected on the instructor interface 500 in FIG. 8. In such embodiments, to generate the arrow for display on the user interface 1000, the user electronic device 102 may determine, based on the identifier, the direction of the arrow 601 from the perspective of the camera 106 in the default pose of the camera 106. For example, the user electronic device 102 may look up, in a database, the direction of the arrow corresponding to the received identifier from the perspective of the camera 106 in the default pose of the camera 106. The user electronic device 102 may then use the transformation to determine how to change the direction of the arrows 1001 (e.g., rotation and/or tilting) from the perspective of the camera 106 such that the arrows 1001 are shown in the user AR interface 1110 as pointing in substantially the same direction from the perspective of the ultrasound imaging device 114 that they would in the default pose.

The user AR interface 1100 shows threes arrow 1001 corresponding to the instruction received from the instructor electronic device 122. The arrows 1001 all point in the same direction, and some of the arrows 1001 have different sizes. Generating for display multiple arrows 1001 corresponding to the received instruction may help to visually show the received instruction in a clear manner. In some embodiments, the user AR interface 1100 may show only one arrow 1001, or any other number of arrows 1001 more than one, such as two, four, five, etc.

Figure 12:
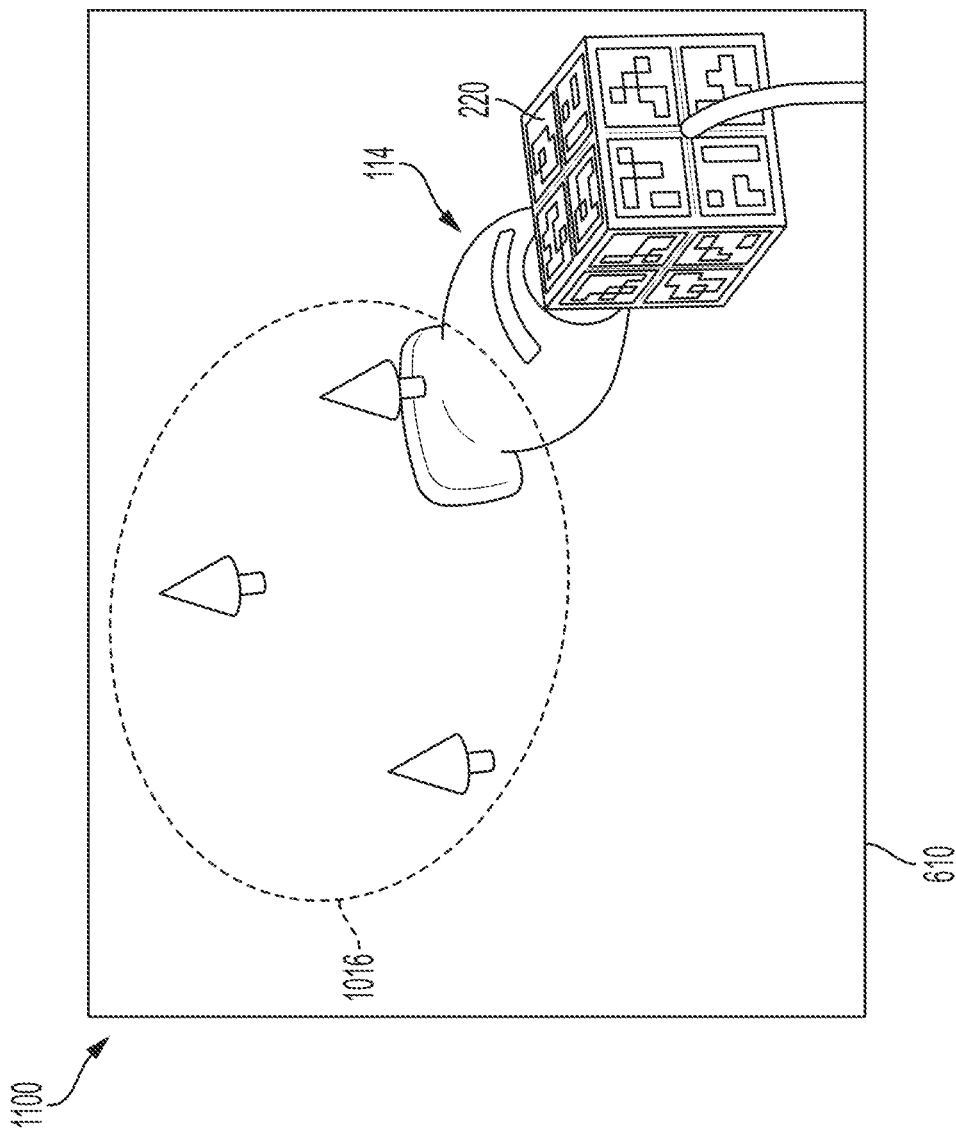
FIGS. 12 and 13 illustrate examples of the user AR interface at two different times.
Figure 13:
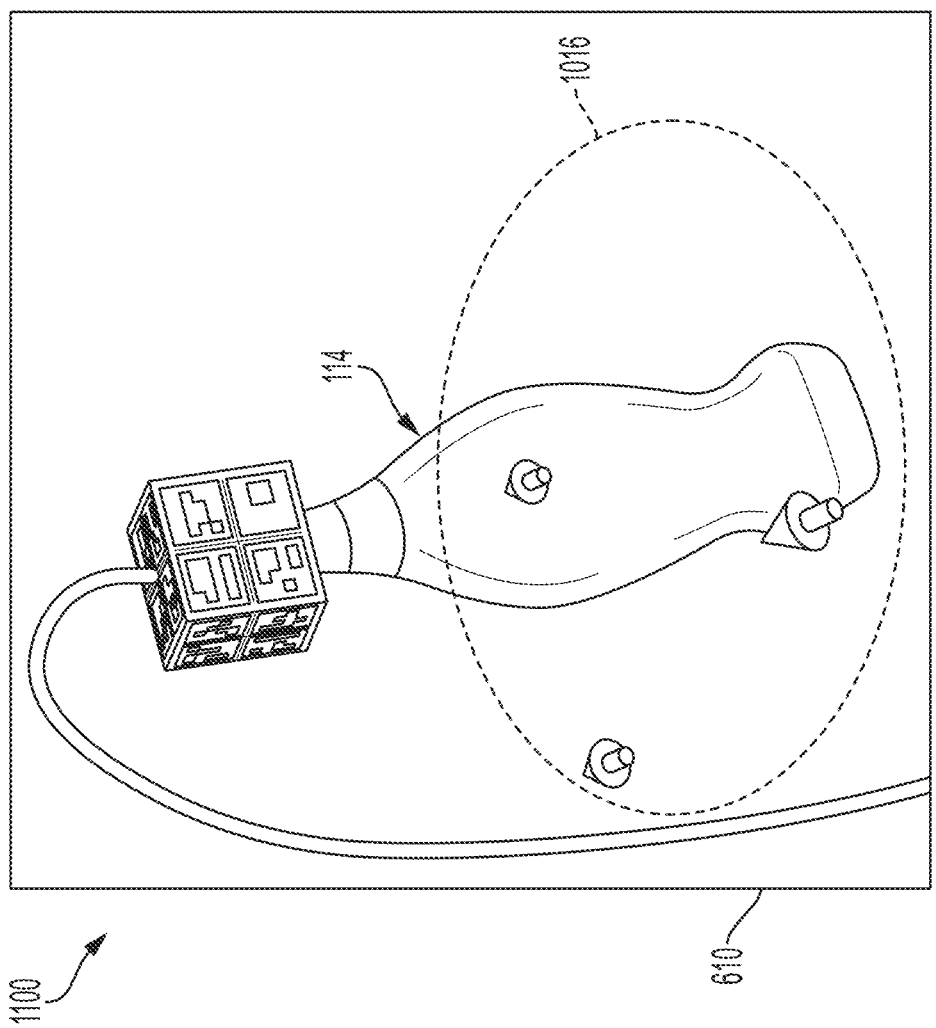

FIGS. 12 and 13 illustrate examples of the user AR interface 1100 at two different times. The AR interface 1100 in FIG. 12 shows a frame of the video 610 captured by the camera 106 at a first time. The frame of the video 610 shows the ultrasound imaging device 114. A fiducial marker 220 that is coupled to the ultrasound imaging device 114 is visible in the frame of the video 610 (as are other fiducial markers not discussed). The user electronic device 102 may determine a transformation from a default pose to the current pose of the camera 106 relative to the ultrasound imaging device 114 and use the transformation to generate arrows 1016 that appear in the AR interface 1100 to be normal to the fiducial marker 220 and to face the same direction as the fiducial marker 220. The arrows 1016 may be helpful as an instruction translate the ultrasound imaging device 114 in the direction that the fiducial marker 220 faces.

The AR interface 1100 in FIG. 13 shows a frame of the video 610 captured by the camera 106 at a second time (e.g., after the first time shown in FIG. 12). The pose of the camera 106 relative to the ultrasound imaging device has changed from the pose in FIG. 12. The user electronic device 102 may determine a transformation from the default pose to the current pose of the camera 106 relative to the ultrasound imaging device 114. The transformation determined at the second time may be different from the transformation determined at the first time. The user electronic device 102 may use the new transformation to generate the arrows 1016 to appear in the AR interface 1100 to be normal to the fiducial marker 220 and to face the same direction as the fiducial marker 220. The arrows 1016 as shown in FIG. 13 therefore may convey the same instruction as the arrows 1016 as shown in FIG. 12, namely to translate the ultrasound imaging device 114 in the direction that the fiducial marker 220 faces, despite the arrows 1016 pointing in different directions from the perspective of the camera 106 in FIGS. 12 and 13. The user electronic device 102 therefore may use the transformations to generate for display the arrows 1016 on the user AR interface 1100 such that the arrows 1016 automatically maintain their direction relative to the ultrasound imaging device 114 even as the camera 106 moves from FIG. 12 to FIG. 13, and therefore may ensure that the instruction conveyed to the user does not change from FIG. 12 to FIG. 13 as the camera 106 moves.

Figure 14:
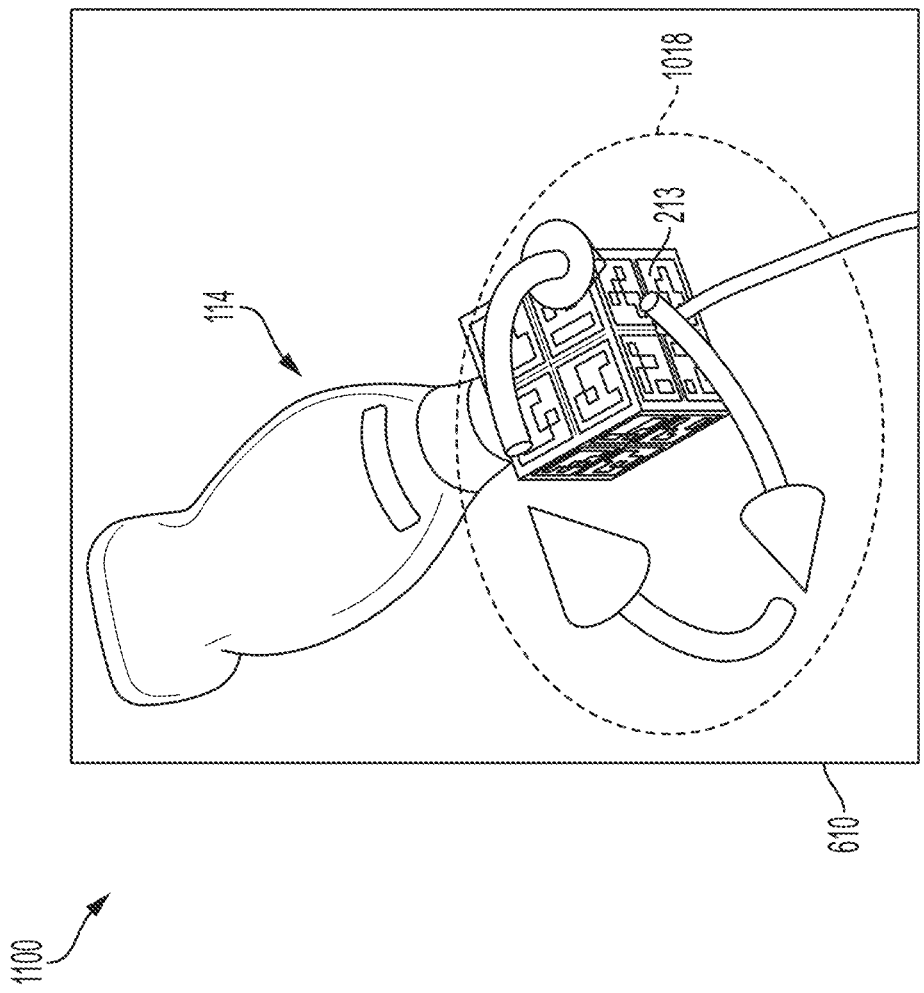
FIGS. 14 and 15 illustrate additional examples of the user AR interface at two different times.
Figure 15:
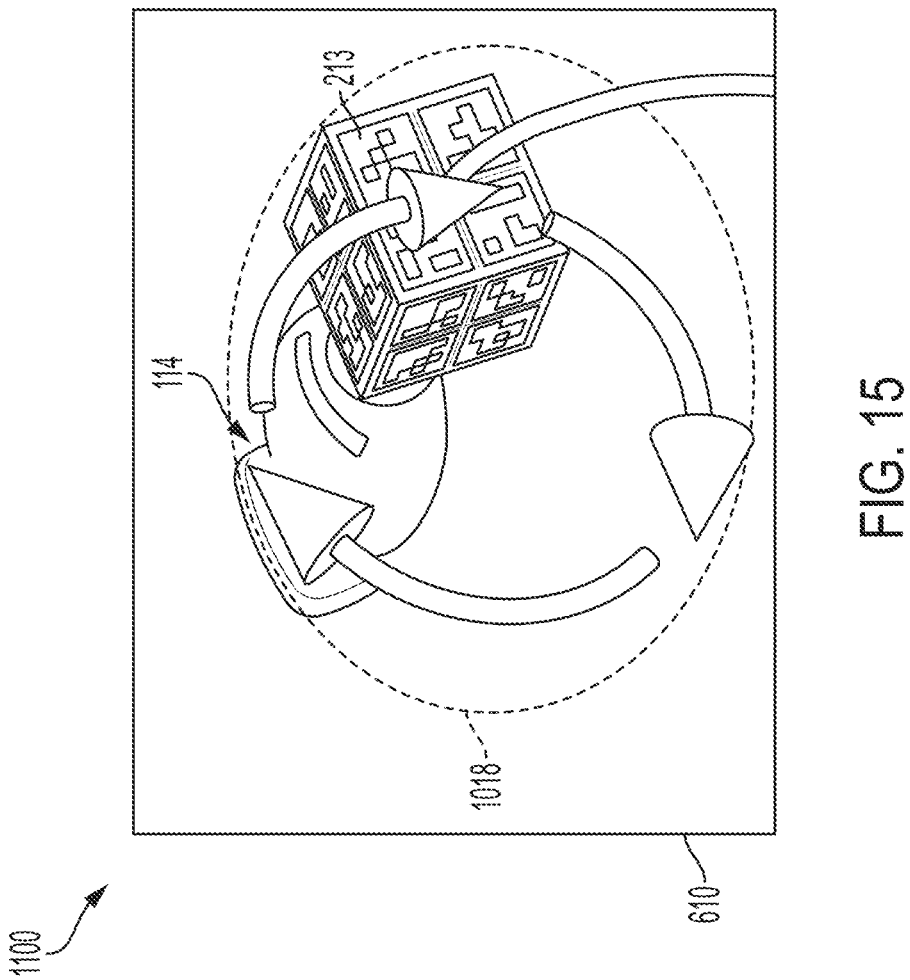

FIGS. 14 and 15 illustrate examples of the user AR interface 1100 at two different times. The AR interface 1100 in FIG. 14 shows a frame of the video 610 captured by the camera 106 at a first time. The frame of the video 610 shows the ultrasound imaging device 114. The fiducial marker 213 that is coupled to the ultrasound imaging device 114 is visible in the frame of the video 610 (as are other fiducial markers not discussed). The user electronic device 102 may determine a transformation from a default pose to the current pose of the camera 106 relative to the ultrasound imaging device 114 and use the transformation to generate arrows 1018 to appear in the user AR interface 1100 to form a circular path parallel to the plane of the fiducial marker 213. The arrows 1018 may be helpful as an instruction rotate the ultrasound imaging device 114 in the direction shown by the arrows 1018.

The AR interface 1100 in FIG. 15 shows a frame of the video 610 captured by the camera 106 at a second time (e.g., after the first time shown in FIG. 14). The pose of the camera 106 relative to the ultrasound imaging device has changed from the pose in FIG. 14. The user electronic device 102 may determine a transformation from the default pose to the current pose of the camera 106 relative to the ultrasound imaging device 114. The transformation determined at the second time may be different from the transformation determined at the first time. The user electronic device 102 may use the new transformation to generate the arrows 1018 to appear in the user AR interface 1100 to form a circular path parallel to the plane of the fiducial marker 213. The arrows 1018 as shown in FIG. 14 therefore may convey the same instruction as the arrows 1018 as shown in FIG. 15, namely to rotate the ultrasound imaging device 114 in the direction shown by the arrows 1018, despite the arrows 1018 pointing in different directions from the perspective of the camera 106 in FIGS. 14 and 15. The user electronic device 102 therefore may use the transformations to generate for display the arrows 1018 on the user AR interface 1100 such that the arrows 1018 automatically maintain their direction relative to the ultrasound imaging, and therefore may ensure that the instruction conveyed to the user does not change from FIG. 14 to FIG. 15 as the camera 106 moves.

Figure 16:
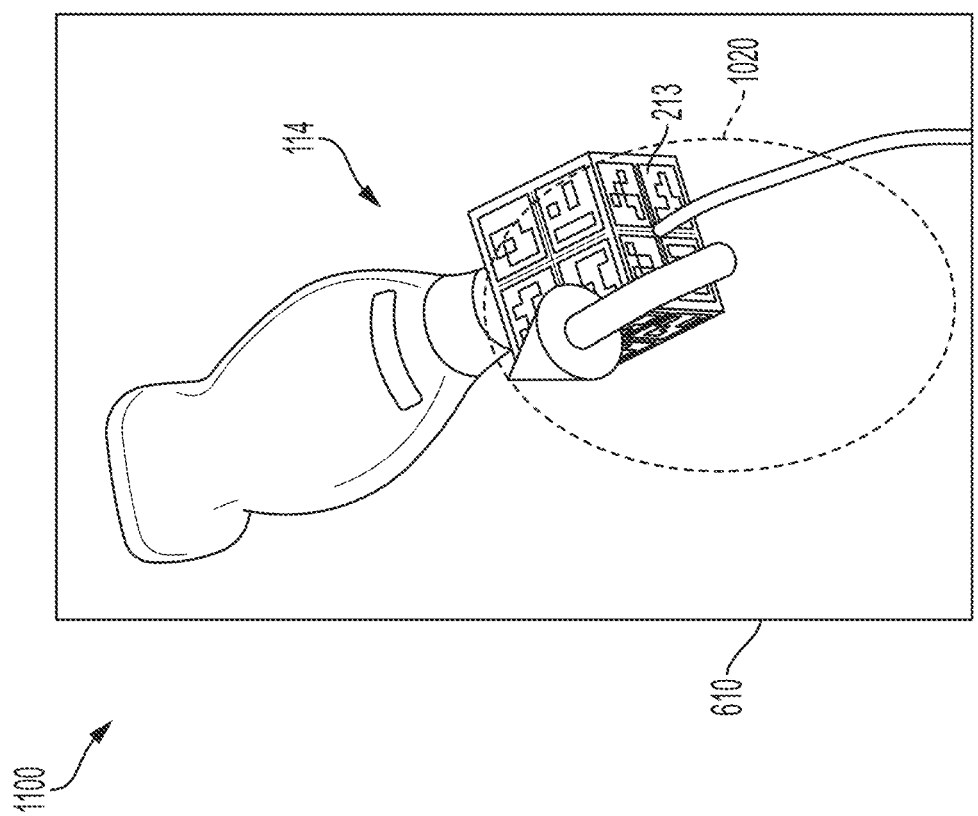
FIGS. 16 and 17 illustrate additional examples of the user AR interface at two different times.
Figure 17:
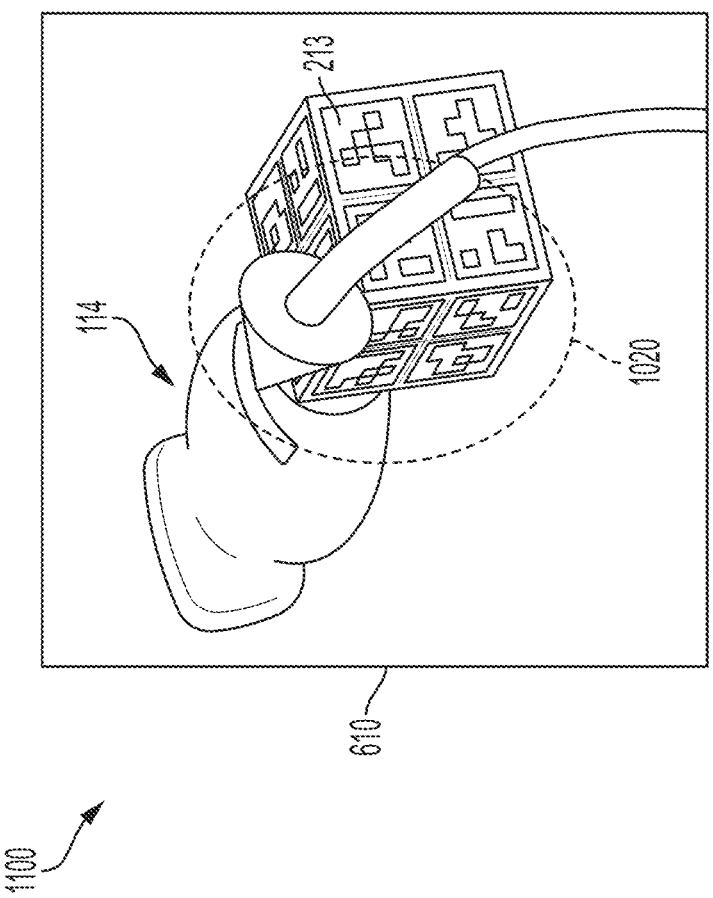

FIGS. 16 and 17 illustrate examples of the user AR interface 1100 at two different times. The AR interface 1100 in FIG. 16 shows a frame of the video 610 captured by the camera 106 at a first time. The frame of the video 610 shows the ultrasound imaging device 114. The fiducial marker 213 that is coupled to the ultrasound imaging device 114 is visible in the frame of the video 610 (as are other fiducial markers not discussed). The user electronic device 102 may determine a transformation from a default pose to the current pose of the camera 106 relative to the ultrasound imaging device 114 and use the transformation to generate arrows 1020 to appear in the user AR interface 1100 to form a circular path orthogonal to a plane of the fiducial marker 213. The arrows 1020 may be helpful as an instruction tilt the ultrasound imaging device 114 in the direction shown by the arrows 1020.

The AR interface 1100 in FIG. 17 shows a frame of the video 610 captured by the camera 106 at a second time (e.g., after the first time shown in FIG. 16). The pose of the camera 106 relative to the ultrasound imaging device has changed from the pose in FIG. 16. The user electronic device 102 may determine a transformation from the default pose to the current pose of the camera 106 relative to the ultrasound imaging device 114. The transformation determined at the second time may be different from the transformation determined at the first time. The user electronic device 102 may use the new transformation to generate the arrows 1020 to appear in the user AR interface 1100 to form a circular path orthogonal to the plane of the fiducial marker 213. The arrows 1020 as shown in FIG. 17 therefore may convey the same instruction as the arrows 1020 as shown in FIG. 15, namely to tilt the ultrasound imaging device 114 in the direction shown by the arrows 1020, despite the arrows 1020 pointing in different directions from the perspective of the camera 106 in FIGS. 16 and 17. The user electronic device 102 therefore may use the transformations to generate for display the arrows 1020 on the user AR interface 1100 such that the arrows 1020 automatically maintain their direction relative to the ultrasound imaging, and therefore may ensure that the instruction conveyed to the user does not change from FIG. 16 to FIG. 17 as the camera 106 moves.

The inventors have recognized that instructing a user to move an ultrasound imaging device may involve the user needing to reconcile the pose of the ultrasound imaging device with the user's own pose. For example, consider a display showing an instruction constituting an image of an ultrasound imaging device and an arrow pointing away from a particular face of the ultrasound imaging device. In particular, consider that the particular face of the ultrasound imaging device is on the right side of the ultrasound imaging device as shown in the image, and the arrow is therefore pointing to the right. Depending on the pose of the user relative to the ultrasound imaging device, it is possible that the particular face of the ultrasound imaging device shown in the image may be on the user's left. Thus, the user may need to reconcile his or her own pose relative to the ultrasound imaging device and determine that following the instruction means moving the ultrasound imaging device to his or her left, despite the arrow in the instruction pointing to the right.

The inventors have recognized that it may be possible to automatically reconcile the pose of the ultrasound imaging device with the user's own pose. If the user's is holding the user electronic device 102 and viewing the user AR interface 1100 captured by the user electronic device 102's camera 106, then the pose of the user may be the same or similar to the pose of the camera 106. As discussed above, the user electronic device 102 may automatically calculate transformations based on poses of the camera 106 relative to the ultrasound imaging device 114 as the camera 106 moves. The user electronic device 102 may then use this transformation to generate for display an arrow on the user AR interface 1100 that automatically maintains its direction relative to the ultrasound imaging device 114 even as the camera 106 and the user move. For example, consider the user AR interface 1100 showing an arrow pointing away from a particular face of the ultrasound imaging device 114, where the arrow points to the right in the user AR interface 1100 (from the perspective of the camera 106). Because the user AR interface 1100 shows the frame of the video 610 captured by the camera 106, and because the camera 106's perspective is the same or similar to the user' perspective, then the particular face of the ultrasound imaging device 114 may be on the user's right and the user may be able to follow this instruction by moving the ultrasound imaging device 114 to his or her right, which is the same direction the arrow points in the user AR interface 1100. If the user and the camera 106 move such that the particular face of the ultrasound imaging device 114 now faces the user's left, the user electronic device 102 may calculate a transformation based on the newly captured frame of the video 610 from the camera 106 and use the transformation to change the arrow to point to the left on the user AR interface 1100 (from the perspective of the camera 106). The user may be able to follow the same instruction as before by moving the ultrasound imaging device 114 to his or her left, which is the same direction the arrow points in the user AR interface 1100. Because the user electronic device 102 may automatically reconcile the user's pose with the pose of the ultrasound imaging device 114, the user may not need to perform this reconciliation himself or herself prior to following an instruction shown on the user AR interface 1100.

Figure 18:
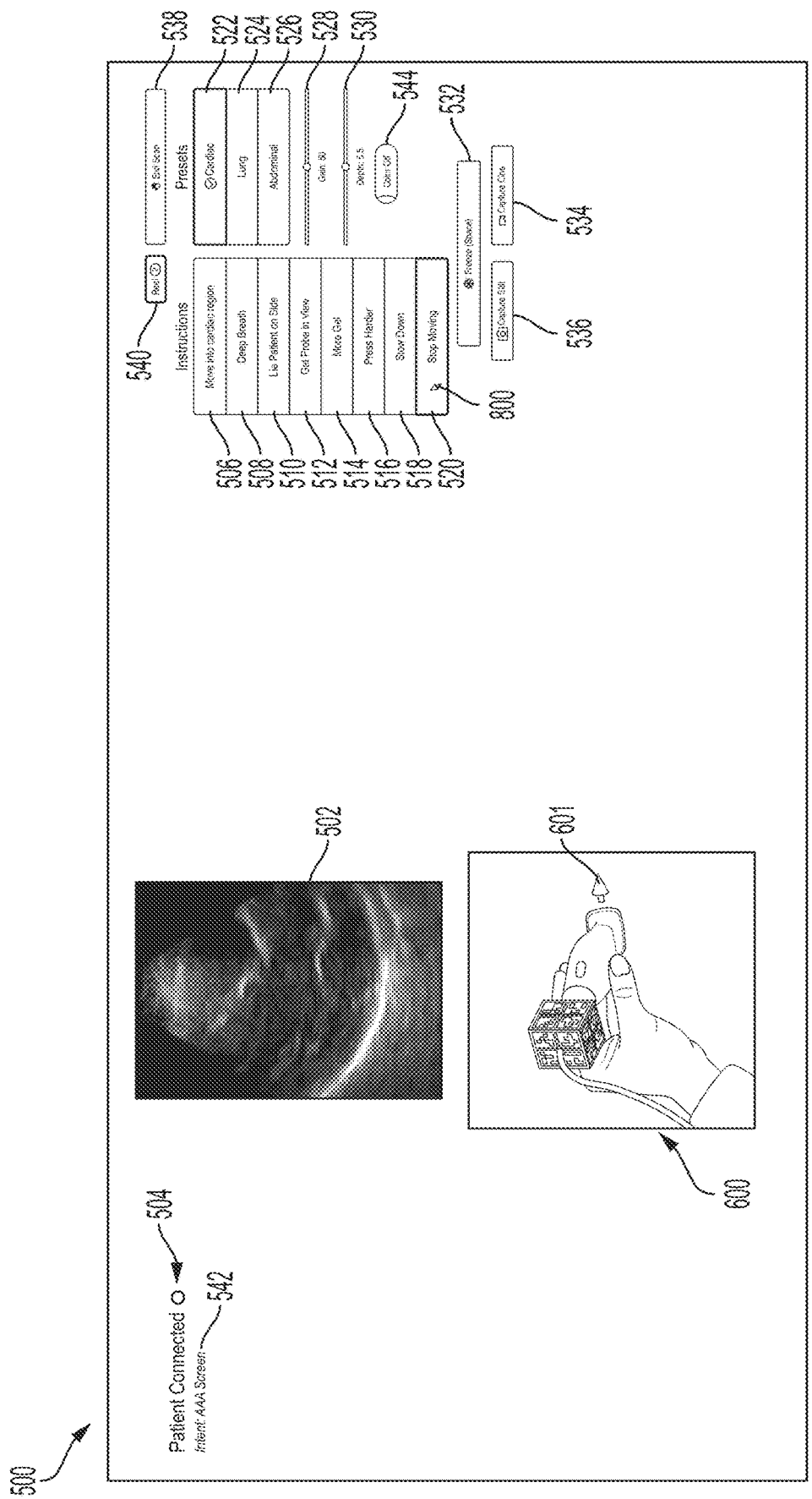
FIG. 18 illustrates the instructor interface of FIG. 5 receiving a selection from an instructor an option to instruct the user to stop moving the ultrasound imaging device.

FIG. 18 illustrates the instructor interface 500 receiving from the instructor a selection of the option 520 to instruct the user to stop moving the ultrasound imaging device 114. For example, the instructor may select this option using the mouse cursor 800. In some embodiments, after the instructor electronic device 122 has received the selection of the arrow 601 on the instructor AR interface 600 and transmitted an indication of the selected arrow 601 to the user electronic device 102, the user electronic device 102 may generate for display the arrows 1001 corresponding to the selected arrow 601, as shown in FIG. 11, indefinitely. In such embodiments, upon receiving the selection of the option 520, as shown in FIG. 18, the instructor electronic device 122 may transmit to the user electronic device 102 an instruction for the user to stop moving the ultrasound imaging device 114. In some embodiments, upon receiving this instruction, the user electronic device 102 may cease to generate for display the instruction for moving the ultrasound imaging device 114 (i.e., the arrows 1001). In some embodiments, upon receiving this instruction, the user electronic device 102 may generate for display text instructing the user to stop moving the ultrasound imaging device 114, such as "Stop moving" or any other text with similar meaning. In some embodiments, upon receiving the selection of the option 520, the instructor electronic device 122 may resume showing all the arrows 601-608 corresponding to possible instructions for moving the ultrasound imaging device 114, so that the instructor may select a new instruction.

In some embodiments, after the instructor electronic device 122 has received the selection of the arrow 601 by the instructor on the instructor AR interface 600 and transmitted an indication of the selected arrow 601 to the user electronic device 102, the user electronic device 102 may generate for display the arrows 1001 corresponding to the selected arrow 601, as shown in FIG. 10, for a set period of time. For example, the set period of time may be 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, or any other suitable period of time. In such embodiments, after the period of time has elapsed, the user AR interface 1100 may cease to generate for display the instruction for moving the ultrasound imaging device 114 (i.e., the arrows 1001), and the instructor AR interface 600 may resume showing all the arrows 601-608 corresponding to possible instructions for moving the ultrasound imaging device 114, so that the instructor may select a new instruction.

In some embodiments, the instructor electronic device 122 may receive a continuous selection of the arrow 601 for a period of time. For example, the instructor may hold down a mouse button while hovering a mouse cursor over the arrow 601, or maintain contact with the arrow 601 by continuously contacting touch-enabled sensors on the display screen 128 of the instructor electronic device 122, for a period of time. In such embodiments, upon receiving the continuous selection, the instructor electronic device 122 may transmit an indication of the arrow 601 to the user electronic device 102, and the user electronic device 102 may generate for display the arrows 1001. Upon detecting cessation of the continuous selection, the instructor electronic device 122 may transmit an instruction to stop moving the ultrasound imaging device 114 to the user electronic device 102, and upon receiving the instruction, the user electronic device 102 may cease to generate for display the arrows 1001. Accordingly, based on the amount of time that the user continuously selects the arrow 601, the instructor may instruct the user to move the ultrasound imaging device 114 in the direction indicated by the arrow for the amount of time and stop moving the ultrasound imaging device 114 after the amount of time has elapsed.

Referring back to FIG. 5, in some embodiments, the text shown by the option 506 to instruct the user to move the ultrasound imaging device 114 into a particular anatomical region of the subject may depend on whether the cardiac preset option 522, the lung preset option 524, or the abdominal preset option 526 is selected. For example, in FIG. 5, the cardiac preset option 522 is selected, and therefore the text shown by the option 506 is "Move into cardiac region." If the lung preset option 524 were selected, the text shown by the option 506 may be "Move into lung region." If the abdominal preset option 526 were selected, the text shown by the option 506 may be "Move into abdominal region."

In some embodiments, upon the instructor electronic device 122 receiving a selection from the instructor of the option 506 to move the ultrasound imaging device 114 into a particular anatomical region, the instructor electronic device 122 may transmit to the user electronic device 102 an instruction for the user to move the ultrasound imaging device 114 into the particular anatomical region. Upon receiving the instruction for the user to move the ultrasound imaging device 114 into the particular anatomical region, the user electronic device 102 may generate for display text instructing the user to move the ultrasound imaging device 114 into the particular anatomical region. For example, the text may be "Move the probe to X region," or other text with a similar meaning, where "X" may be "cardiac," "lung," or "abdominal" depending on whether the cardiac preset option 522, the lung preset option 524, or the abdominal preset option 526 has been selected.

In some embodiments, the instructor may select, on the instructor electronic device 122, from a menu of predefined anatomical views (e.g., parasternal long axis view of the heart). Upon selection of one of the predefined views, a cartoon of a body showing a marker indicating where to position the ultrasound imaging device 114 to collect the predefined view may be transmitted to and displayed on the user electronic device 102. The cartoon may be displayed in conjunction with the text discussed above to move the ultrasound imaging device 114 into a particular anatomical region. The cartoon may be displayed along with text for positioning the subject (e.g., "Position patient on left side"). In some embodiments, the instructor may create, on the instructor electronic device 122, a custom cartoon. In particular, the instructor may select a location on a cartoon of a body to place a marker indicating where to position the ultrasound imaging device 114 to collect a particular anatomical view. The instructor may also select positioning information. The custom cartoon and the positioning information may then be transmitted to and displayed on the user electronic device 102.

In some embodiments, upon the instructor electronic device 122 receiving a selection from the instructor of the option 508 to instruct the user to instruct the subject to take and hold a deep breath, the instructor electronic device 122 may transmit to the user electronic device 102 an instruction for the user to instruct the subject to take and hold a deep breath. Upon receiving the instruction for the user to instruct the subject to take and hold a deep breath, the user electronic device 102 may generate for display text instructing the user to instruct the subject to take and hold a deep breath. For example, the text may be "Deep breath," "Tell patient to take and hold a deep breath," or other text with a similar meaning.

In some embodiments, upon the instructor electronic device 122 receiving a selection from the instructor of the option 510 to instruct the user to instruct the subject to lie on his or her side, the instructor electronic device 122 may transmit to the user electronic device 102 an instruction for the user to instruct the user to instruct the subject to lie on his or her side. Upon receiving the instruction for the user to instruct the user to instruct the subject to lie on his or her side, the user electronic device 102 may generate for display text instructing the user to instruct the user to instruct the subject to lie on his or her side. For example, the text may be "Lie on side," "Lie patient on side," "Tell patient to lie on side," or other text with a similar meaning.

In some embodiments, upon receiving a selection on the instructor electronic device 122 of the option 512 to instruct the user to move the ultrasound imaging device 114 into the view of the camera 106 (i.e., the camera 106 capturing the frame of the video 610), the instructor electronic device 122 may transmit to the user electronic device 102 an instruction for the user to move the ultrasound imaging device 114 into the view of the camera 106. Upon receiving the instruction for the user to move the ultrasound imaging device 114 into the view of the camera 106, the user electronic device 102 may generate for display text instructing the user to move the ultrasound imaging device 114 into the view of the camera 106. For example, the text may be "Camera cannot see probe. Please move probe into view," "Move the probe into view of camera," or other text with a similar meaning.

In some embodiments, the user electronic device 102 may automatically generate for display text instructing the user to move the ultrasound imaging device 114 into the view of the camera 106. For example, the user electronic device 102 may generate the text upon failing to detect fiducial markers in a frame of the video 610 that depicts the ultrasound imaging device 114 and is captured by the camera 106.

In some embodiments, upon the instructor electronic device 122 receiving a selection from the instructor of the option 514 to instruct the user to apply more gel to the subject, the instructor electronic device 122 may transmit to the user electronic device 102 an instruction for the user to apply more gel to the subject. Upon receiving the instruction for the user to apply more gel to the subject, the user electronic device 102 may generate for display text instructing the user to apply more gel to the subject. For example, the text may be "Apply gel," or other text with a similar meaning.

In some embodiments, upon the instructor electronic device 122 receiving a selection from the instructor of the option 516 to instruct the user to press the ultrasound imaging device 114 harder onto the subject, the instructor electronic device 122 may transmit to the user electronic device 102 an instruction for the user to press the ultrasound imaging device 114 harder onto the subject. Upon receiving the instruction for the user to press the ultrasound imaging device 114 harder onto the subject, the user electronic device 102 may generate for display text instructing the user to press the ultrasound imaging device 114 harder onto the subject. For example, the text may be "Press harder," or other text with a similar meaning.

In some embodiments, upon the instructor electronic device 122 receiving a selection from the instructor of the option 518 to instruct the user to move the ultrasound imaging device 114 in shorter and/or smaller increments, the instructor electronic device 122 may transmit to the user electronic device 102 an instruction for the user to move the ultrasound imaging device 114 in shorter and/or smaller increments. Upon receiving the instruction for the user to move the ultrasound imaging device 114 in shorter and/or smaller increments, the user electronic device 102 may generate for display text instructing the user to move the ultrasound imaging device 114 in shorter and/or smaller increments. For example, the text may be "Slow down," "Move slower," "Move in smaller increments," "Move in shorter increments," or other text with a similar meaning.

As discussed above, selection at the instructor electronic device of the options 506, 508, 510, 512, 514, 516, 518, and/or 520 may result in the user electronic device 102 generating text for display. The text may be displayed on the user electronic device 102, for a default duration, a custom duration, until a reset option is chosen at the instructor electronic device 122, or until another option is chosen at the instructor electronic device 122.

In some embodiments, upon the instructor electronic device 122 receiving a selection from the instructor of the cardiac preset option 522, the instructor electronic device 122 may transmit to the user electronic device 102 an instruction to change the imaging preset to a cardiac preset. Upon receiving the instruction to change the imaging preset to a cardiac preset, the user electronic device 102 may change the imaging preset to a cardiac preset, for example, by transmitting a command to the ultrasound imaging device 114 to configure the ultrasound imaging device 114 with imaging parameters corresponding to a cardiac preset.

In some embodiments, upon the instructor electronic device 122 receiving a selection from the instructor of the lung preset option 524, the instructor electronic device 122 may transmit to the user electronic device 102 an instruction to change the imaging preset to a lung preset. Upon receiving the instruction to change the imaging preset to a lung preset, the user electronic device 102 may change the imaging preset to a lung preset, for example, by transmitting a command to the ultrasound imaging device 114 to configure the ultrasound imaging device 114 with imaging parameters corresponding to a lung preset.

In some embodiments, upon the instructor electronic device 122 receiving a selection from the instructor of the abdominal preset option 526, the instructor electronic device 122 may transmit to the user electronic device 102 an instruction to change the imaging preset to an abdominal preset. Upon receiving the instruction to change the imaging preset to an abdominal preset, the user electronic device 102 may change the imaging preset to an abdominal preset for example, by transmitting a command to the ultrasound imaging device 114 to configure the ultrasound imaging device 114 with imaging parameters corresponding to an abdominal preset.

In some embodiments, upon the instructor electronic device 122 receiving a selection from the instructor of a particular gain value from the gain slider 528, the instructor electronic device 122 may transmit to the user electronic device 102 an instruction to change the imaging gain to the particular gain value. Upon receiving the instruction to change the imaging gain to the particular gain value, the user electronic device 102 may change the imaging gain to the particular gain value, for example, by configuring itself to generate ultrasound images using the particular gain, and/or by transmitting a command to the ultrasound imaging device 114 to generate ultrasound images using the particular gain value.

In some embodiments, upon the instructor electronic device 122 receiving a selection from the instructor of a particular depth value from the depth slider 530, the instructor electronic device 122 may transmit to the user electronic device 102 an instruction to change the imaging depth to the particular depth value. Upon receiving the instruction to change the imaging depth to the particular depth value, the user electronic device 102 may change the imaging depth to the particular depth value, for example, by transmitting a command to the ultrasound imaging device 114 to collect ultrasound data down to the particular depth.

In some embodiments, upon the instructor electronic device 122 receiving a selection from the instructor of a particular gain value from the gain slider 528, the instructor electronic device 122 may transmit to the user electronic device 102 an instruction to generate ultrasound images using the particular gain value. Upon receiving the instruction to generate ultrasound images using the particular gain value, the user electronic device 102 may configure itself to generate ultrasound images using the particular gain, and/or transmit a command to the ultrasound imaging device 114 to generate ultrasound images using the particular gain value.

In some embodiments, upon the instructor electronic device 122 receiving a selection from the instructor to turn on a Color Doppler mode from the color option 544, the instructor electronic device 122 may transmit to the user electronic device 102 an instruction to turn on a Color Doppler mode. Upon receiving the instruction to turn on a Color Doppler mode, the user electronic device 102 may generate ultrasound images using a Color Doppler mode. In some embodiments, upon the instructor electronic device 122 receiving a selection from the instructor a selection to turn off a Color Doppler mode from the color option 544, the instructor electronic device 122 may transmit to the user electronic device 102 an instruction to turn off Color Doppler mode. Upon receiving the instruction to turn off a Color Doppler mode, the user electronic device 102 may turn off a Color Doppler mode. In some embodiments, the instructor may use controls on the instructor interface 500 to manipulate vertices of a color box on the ultrasound image 502 to select on which portions of the ultrasound image 502 Color Doppler mode should be activated.

In some embodiments, upon the instructor electronic device 122 receiving a selection from the instructor of the freeze option 532, the instructor electronic device 122 may transmit to the user electronic device 102 an instruction to freeze ultrasound images on the user interface 1000. Upon receiving the instruction to freeze ultrasound images on the user interface 1000, the user electronic device 102 may not update the ultrasound image 502 shown on the user interface 1000 using ultrasound images generated from new ultrasound data. Similarly, the user electronic device 102 may not transmit ultrasound images generated from new ultrasound data to the instructor electronic device 122 so that the instructor interface will not update the ultrasound image 502 shown on the instructor interface 500. Upon selection of the freeze option 532, the instructor interface 500 may show an interface from which the instructor may scroll through and view ultrasound images/cines that have been previously saved to memory. The instructor may use controls on the instructor interface 500 to annotate these ultrasound images/cines.

In some embodiments, upon the instructor electronic device 122 receiving a selection from the instructor of the still capture option 536, the instructor electronic device 122 may transmit to the user electronic device 102 an instruction to save the most recently generated ultrasound image to memory. Upon receiving the instruction to save the most recently generated ultrasound image to memory, the user electronic device 102 may save the most recently generated ultrasound image to the memory 112 on the user electronic device 102, and/or transmit the ultrasound image to the one or more servers 134 for storage in memory at the one or more servers 134. In some embodiments, upon the instructor electronic device 122 receiving a selection from the instructor of the still capture option 536, the instructor electronic device 122 may save the ultrasound image most recently received at the instructor electronic device 122 from the user electronic device 102, and/or transmit the ultrasound image to the one or more servers 134 for storage in memory at the one or more servers 134. It should be noted that the most recently generated ultrasound image, the ultrasound image most recently received at the instructor electronic device 122 from the user electronic device 102, and the ultrasound image 502 currently shown on the user interface 1000 and the instructor interface 500 may not necessarily be the same if there are lag times, for example, between generation, transmission, and display of an ultrasound image. In some embodiments, upon the instructor electronic device 122 receiving a selection from the instructor of the still capture option 536, both the instructor electronic device 122 and the user electronic device 102 may save ultrasound image(s) to memory in a synchronized or overlapping fashion (e.g., the instructor electronic device 122 and the user electronic device 102 may save the same ultrasound image(s) or sets of ultrasound images containing overlapping ultrasound images).

In some embodiments, the cine capture option 534 may have two states, an enabled state and a disabled state. When the cine capture option 534 is in the enabled state, selection of the cine capture option 534 may cause the cine capture option 534 to enter the disable state. When the cine capture option 534 is in the disabled state, selection of the cine capture option 534 may cause the cine capture option 534 to enter the enabled state. When the cine capture option 534 is in the enabled state, the cine capture option 534 may appear differently on the instructor interface 500 than when the cine capture option 534 is in the disabled state. For example, when the cine capture option 534 is in the enabled state, the cine capture option 534 may appear as a depressed button, while when the cine capture option 534 is in the disabled state, the cine capture option 534 may appear as an unpressed button. As another option, the cine capture option 534 may be different colors depending on whether the cine capture option 534 is in the enabled state or the disabled state. In some embodiments, upon the instructor electronic device 122 receiving a selection from the instructor of the cine capture option 534 such that the cine capture option 534 enters the enabled state, the instructor electronic device 122 may transmit to the user electronic device 102 an instruction to save a cine (i.e., one or more ultrasound images in a series). Upon receiving the instruction to save a cine of ultrasound images, the user electronic device 102 may save ultrasound images that are generated based on new ultrasound data. In other words, as new ultrasound data is collected by the ultrasound imaging device 114, and new ultrasound images are generated based on the new ultrasound data, the user electronic device 102 may save the new ultrasound images to the memory 112 on the user electronic device 102, and/or transmit the new ultrasound image to the one or more servers 134 for storage in memory at the one or more servers 134. In some embodiments, upon selection of the cine capture option 534 such that the cine capture option 534 enters the disabled state, the instructor electronic device 122 may transmit to the user electronic device 102 an instruction to stop capturing a cine of ultrasound images. Upon receiving the instruction to stop capturing a cine of ultrasound images, the user electronic device 102 may stop saving ultrasound images that are generated based on new ultrasound data.

In some embodiments, upon the instructor electronic device 122 receiving a selection from the instructor of the cine capture option 534 such that the cine capture option 534 enters the enabled state, the instructor electronic device 122 may save ultrasound images that are generated based on new ultrasound data and received from the user electronic device 102. In other words, as new ultrasound data is collected by the ultrasound imaging device 114, and new ultrasound images are generated based on the new ultrasound data, the user electronic device 102 may transmit the new ultrasound images to the instructor electronic device 122, and the instructor electronic device 122 may save the new ultrasound images in the memory 132 on the instructor electronic device 122, and/or transmit the new ultrasound image to the one or more servers 134 for storage in memory at the one or more servers 134. In some embodiments, upon selection of the cine capture option 534 such that the cine capture option 534 enters the disabled state, the instructor electronic device 122 may stop saving ultrasound images that are generated based on new ultrasound data.

In some embodiments, upon the instructor electronic device 122 receiving a selection from the instructor of the end scan option 538, the instructor electronic device 122 may transmit to the user electronic device 102 an instruction to end the ultrasound scan. Upon receiving the instruction to end the ultrasound scan, the user electronic device 102 may transmit to the ultrasound imaging device 114 a command to stop collecting ultrasound data.

The patient connection indicator 504 may indicate whether the user electronic device 102 has established a communication link with the instructor electronic device 122 over the network 116. The intent indicator 542 may indicate the goal of the current imaging session. For example, the intent indicator 542 in FIG. 5 indicates that the intent of the current imaging session is to screen for abdominal aortic aneurysm. The reel indicator 540 may indicate a number of ultrasound images/cines that have been saved. Upon selection of the reel indicator 540, the instructor interface 500 may show the saved ultrasound images/cines. Selecting a saved ultrasound image/cine may expand the ultrasound image/cine while the rest of the instructor interface 500 is darkened for easier viewing. In some embodiments, the instructor interface 500 may include an interface from which the instructor may create a report including saved ultrasound images/cines.

In some embodiments, the instructor interface 500 may have additional controls for the instructor to perform measurements on an ultrasound image 502 displayed on the instructor interface 500. For example, the instructor may use the controls to measure anatomical parameters (e.g., the diameter of a blood vessel) or a physiological parameter (e.g., ejection fraction).

Selection of any of the options on the instructor interface 500 may be performed on the instructor electronic device 122 using the input device 128, which may include using a mouse, a touch-screen, a keyboard, voice input, a 3D mouse (e.g., a SpaceMouse®), a microphone, a controller using gesture recognition (e.g., a Leap Motion® controller), or any other means of input.

Referring back to FIG. 10, in some embodiments, upon the user electronic device 102 receiving a selection from the user of the still capture option 1008, the user electronic device 102 may save the ultrasound image 502 currently shown on the user interface 1000 to the memory 112 on the user electronic device 102, and/or transmit the ultrasound image 502 to the one or more servers 134 for storage in memory at the one or more servers 134. In some embodiments, upon the user electronic device 102 receiving a selection from the user of the still capture option 1008, the user electronic device 102 may save the most recently generated ultrasound image to the memory 112 on the user electronic device 102, and/or transmit the ultrasound image 502 to the one or more servers 134 for storage in memory at the one or more servers 134. It should be noted that the most recently generated ultrasound image may not necessarily be the ultrasound image 502 currently shown on the user interface 1000 if there are lag times, for example, between generation of an ultrasound image and displaying the ultrasound image.

In some embodiments, the cine capture option 1010 may have two states, an enabled state and a disabled state. When the cine capture option 1010 is in the enabled state, selection of the cine capture option 1010 may cause the cine capture option 1010 to enter the disable state. When the cine capture option 1010 is in the disabled state, selection of the cine capture option 1010 may cause the cine capture option 1010 to enter the enabled state. When the cine capture option 1010 is in the enabled state, the cine capture option 1010 may appear differently on the user interface 1000 than when the cine capture option 1010 is in the disabled state. For example, when the cine capture option 1010 is in the enabled state, the cine capture option 1010 may appear as a depressed button, while when the cine capture option 1010 is in the disabled state, the cine capture option 1010 may appear as an unpressed button. As another option, the cine capture option 1010 may be different colors depending on whether the cine capture option 1010 is in the enabled state or the disabled state. In some embodiments, upon selection of the cine capture option 1010 such that the cine capture option 1010 enters the enabled state, the user electronic device 102 may save ultrasound images that are generated based on new ultrasound data. In other words, as new ultrasound data is collected by the ultrasound imaging device 114, and new ultrasound images are generated based on the new ultrasound data, the user electronic device 102 may save the new ultrasound images to the memory 112 on the user electronic device 102, and/or transmit the new ultrasound image to the one or more servers 134 for storage in memory at the one or more servers 134. In some embodiments, upon selection of the cine capture option 1010 such that the cine capture option 534 enters the disabled state, the user electronic device 102 may stop saving ultrasound images that are generated based on new ultrasound data.

The depth scale 1004 may indicate at what depth (beyond the ultrasound imaging device 114) anatomical features shown in the ultrasound image 502 are located. The information panel 1014 may show various information such as an avatar of the current user, thermal index, mechanical index, frame rate, the battery status of the ultrasound imaging device 114, the temperature status of the ultrasound imaging device 114, and the current preset. The reel indicator 1015 may show the number of saved ultrasound images/cines. Upon selection of the reel indicator 1015, the user interface 1000 may show the saved ultrasound images/cines. Selecting a saved ultrasound image/cine may expand the ultrasound image/cine while the rest of the user interface 1000 is darkened for easier viewing. In some embodiments, the user electronic device 102 may not allow a user to certain settings (e.g., imaging parameters) on the user interface 1000. Instead, only the instructor may be able to remotely control these settings.

In some embodiments, the user and the instructor may communicate with voice. For example, if the input device 138 of the instructor electronic device 122 includes a microphone, the instructor may speak into the microphone, the instructor electronic device 122 may transmit the audio signal from the microphone to the user electronic device 102, and the user electronic device 102 may output the audio signal from the speaker 109. If the input device 118 of the user electronic device 102 includes a microphone, the user may speak into the microphone, the user electronic device 102 may transmit the audio signal from the microphone to the instructor electronic device 122, and the instructor electronic device 102 may output the audio signal from the speaker 141. The user and the instructor may use voice communication for further assistance in guiding the user to move the ultrasound imaging device 114.

In some embodiments, the instructor may select a position on the instructor AR interface 600 where the user ought to position the ultrasound imaging device 114. For example, the instructor may drag a translucent image of the ultrasound imaging device 114 on the frame of the video 610 to the desired position. The instructor electronic device 122 may transmit the selected position to the user electronic device 102, and the user electronic device 102 may display the selected position of the user AR interface 1100 for instructing the user where to position the ultrasound imaging device 114.

It should be appreciated that certain of the previous figures (e.g., FIGS. 5, 8, 9, 10, and 18) may not illustrate real situations. In particular, these figures may show a frame of a video 610 depicting an ultrasound imaging device 114 scanning a non-living object, as well as an ultrasound image 502 collected by the ultrasound imaging device 114, where the ultrasound image 502 shows anatomy from a living subject. It should be appreciated that in a real situation, the frame of the video 610 may depict the ultrasound imaging device 114 scanning a living subject and the ultrasound image 502 may show anatomy of the living subject.

Various inventive concepts may be embodied as one or more processes, of which examples are provided hereinafter. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Figure 19:
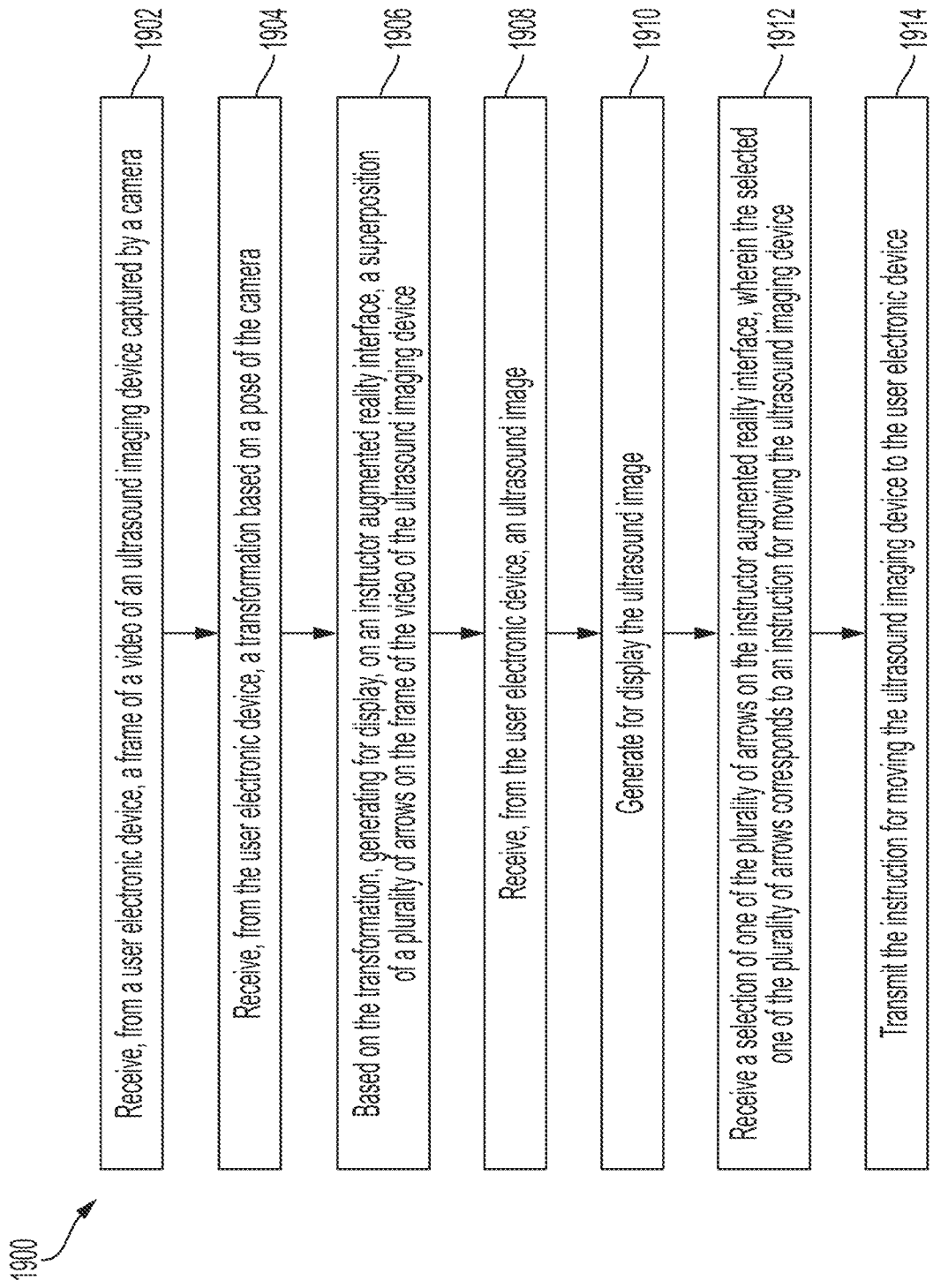
FIG. 19 shows an example process for tele-medicine executable by an instructor electronic device, in accordance with an exemplary embodiment.

FIG. 19 shows an example process 1900 for tele-medicine executable by an instructor electronic device (e.g., instructor electronic device 122), in accordance with an exemplary embodiment. The instructor user electronic device may be associated with a human instructor providing instructions to a user of an ultrasound imaging device (e.g., ultrasound imaging device 114). The instructor electronic device may be in communication (e.g., over a wireless connection) with a user electronic device (e.g., user electronic device 102) associated with a user of the ultrasound imaging device. The instructor electronic device and the user electronic device may be remote from each other.

In act 1902, the instructor electronic device receives, from the user electronic device, a frame of a video (e.g., the frame of the video 610) showing the ultrasound imaging device. The frame of the video may be captured by a camera (e.g., camera 106). For example, if the user electronic device is a mobile phone, the camera may be the mobile phone's camera. The user of the ultrasound imaging device may hold the ultrasound imaging device on a subject being imaged and position the camera of the user electronic device (which the user may also be holding) such that the ultrasound imaging device is in view of the camera. In some embodiments, the user electronic device may continuously capture video throughout the ultrasound imaging session, and the instructor electronic device may continuously receive the video throughout the ultrasound imaging session. The instructor electronic device may receive the video encoded as any suitable form of data for transmission. In some embodiments, the instructor electronic device may receive the video from the user electronic device over a wireless communication link (e.g., over a BLUETOOTH, WiFi, or ZIGBEE wireless communication link). The process 1900 proceeds from act 1902 to act 1904.

In act 1904, the instructor electronic device receives, from the user electronic device, a transformation based on a pose of the camera. In some embodiments, the ultrasound imaging device may include fiducial markers (e.g., ArUco markers) coupled to the ultrasound imaging device, and the transformation may describe a change in pose of the camera from (1) a default pose of the camera relative to the fiducial markers on the ultrasound imaging device to (2) the current pose of the camera relative to the fiducial markers on the ultrasound imaging device when the camera captured the frame of the video. The transformation may include a quantification of translations, rotations, and/or tilts of the camera from the default pose to the current pose, and may be in the form of a matrix. The user electronic device may use pose estimation techniques to analyze a particular frame of the video from a particular time to determine the transformation at the particular time. In embodiments in which the instructor electronic device continuously receives video, the instructor electronic device may continuously receive updated transformations based on the current frame of the video throughout the imaging session. The instructor electronic device may receive the transformation encoded as any suitable form of data for transmission. In some embodiments, the instructor electronic device may receive the transformation from the user electronic device over a wireless communication link (e.g., over a BLUETOOTH, WiFi, or ZIGBEE wireless communication link). The process 1900 proceeds from act 1904 to act 1906.

In act 1906, based on the transformation received in act 1904, the instructor electronic device generates for display, on an instructor augmented reality (AR) interface (e.g., instructor AR interface 600), a superposition of a plurality of arrows (e.g., arrows 601-608) on the frame of the video of the ultrasound imaging device received in act 1902. Accordingly, the instructor AR interface may include both real (the video) and non-real (arrows) components. In embodiments in which the instructor electronic device includes a display screen (e.g., when the instructor electronic device is a mobile phone, tablet, or laptop), the instructor electronic device may generate the instructor AR interface for display on its own display screen. The process 1900 proceeds from act 1906 to act 1908.

The arrows may correspond to possible instructions for moving the ultrasound imaging device, namely instructions to translate, rotate, and/or tilt the ultrasound imaging device. Instructions for moving the ultrasound imaging device may include any combination of instructions to translate the ultrasound imaging device, instructions to rotate the ultrasound imaging device (i.e., rotation about the longitudinal axis of the ultrasound imaging device), and instructions to tilt the ultrasound imaging device (e.g., tilting the ultrasound imaging device about the end portion of the ultrasound imaging device contacting the subject). The instructions to move the ultrasound imaging device may be instructions designed to move the ultrasound imaging device from a current position and orientation to a position and orientation on a subject such that a target anatomical view (e.g., a parasternal long axis view of the heart) can be obtained.

In embodiments in which the ultrasound imaging device includes fiducial markers coupled to the ultrasound imaging device, the transformation describing changes in the pose of the camera relative to the fiducial markers may equivalently describe changes in the pose of the camera relative to the ultrasound imaging device. If the camera or the ultrasound imaging device moves, the transformation may capture that movement. In particular, the transformation may describe how to change the direction of an arrow relative to the camera such that the direction of the arrow relative to the ultrasound imaging device as seen in the instructor AR interface remains constant even if the camera moves relative to the ultrasound imaging device.

In act 1908, the instructor electronic device receives an ultrasound image (e.g., ultrasound image 502) from the user electronic device. The user electronic device may be in communication with the ultrasound imaging device, and in some embodiments, the ultrasound imaging device may collect raw ultrasound data, transmit the raw ultrasound data to the user electronic device, and the user electronic device may generate the ultrasound image from the raw ultrasound data. In some embodiments, the ultrasound imaging device may collect raw ultrasound data, generate the ultrasound image from the raw ultrasound data, and transmit the ultrasound image to the user electronic device. The user electronic device may then transmit the ultrasound image to the instructor electronic device. In some embodiments, the instructor electronic device may receive the ultrasound image from the user electronic device over a wireless communication link (e.g., over a BLUETOOTH, WiFi, or ZIGBEE wireless communication link). The process 1900 proceeds from act 1908 to act 1910.

In act 1910, the instructor electronic device generates the ultrasound image (that was received in act 1908) for display. For example, the instructor electronic device may generate the ultrasound image for display on the instructor electronic device. When new ultrasound data is collected and a new ultrasound image is generated, the user electronic device may transmit the new ultrasound image to the instructor electronic device, and the instructor electronic device may generate the new ultrasound image for display. The process 1900 proceeds from act 1910 to act 1912.

In act 1912, the instructor electronic device receives a selection of one of the plurality of arrows on the instructor AR interface. As discussed above, the arrows superimposed on the video of the ultrasound imaging device correspond to possible instructions for moving the ultrasound imaging device. Accordingly, the selected arrow corresponds to a particular instruction for moving (e.g., translating, rotating, or tilting) the ultrasound imaging device. By selecting the arrow, the instructor may decide that the user should move the ultrasound imaging device in a direction indicated by the arrow in order to move the ultrasound imaging device closer to the target anatomical region. If the instructor AR interface corresponds to the instructor AR interface 600, the instructor electronic device may receive a selection of one of the arrows 601-608. In some embodiments, receiving the selection of one of the arrows may include receiving a mouse click on one of the arrow shown on a display screen. In some embodiments, the instructor electronic device may include a touch-sensitive display screen showing the instructor AR interface, and receiving the selection of one of the arrows may include detecting contact with an arrow shown on the touch-sensitive display screen. The instructor may use the ultrasound image and/or the frame of the video of the ultrasound imaging device to decide how to instruct the user to move the ultrasound imaging device. The process 1900 proceeds from act 1912 to act 1914.

In act 1914, the instructor electronic device transmits the instruction corresponding to the arrow selected in act 1912 to the user electronic device. The instructor electronic device may transmit the instruction encoded as any suitable form of data for transmission. In some embodiments, each of the arrows shown in the instructor AR interface may have an identifier, and the instructor electronic device may transmit the identifier of the selected arrow to the user electronic device. For example, consider an arrow that points right in a default pose of the camera relative to the ultrasound imaging device. As discussed above, as the pose of the camera relative to the ultrasound imaging device changes, the arrow may point in different directions as seen in the video so that the direction of the arrow relative to the ultrasound imaging device may remain substantially constant. At any given time, however, the arrow may be identified as the "right" arrow, based on its direction as seen in the video in the default pose, despite the arrow not necessarily pointing to the right as seen in the video at the given time. If the arrow identified as "right" is selected in act 1912, the instructor electronic device may transmit the instruction corresponding to this arrow may transmitting the identifier "right." In some embodiments, the instructor electronic device may transmit the instruction to the user electronic device over a wireless communication link (e.g., over a BLUETOOTH, WiFi, or ZIGBEE wireless communication link). As will be discussed further with reference to FIG. 20, the instruction transmitted from the instructor electronic device may be generated for display on the user electronic device as an arrow and may be used to instruct the user of the ultrasound imaging device to move the ultrasound imaging device in accordance with the instruction.

It should be noted that the acts of process 1900 may not necessarily proceed in the order shown in FIG. 19. For example, act 1904 may occur before or simultaneously with act 1902, and acts 1908 and 1910 may occur before or simultaneously with acts 1902, 1904, and 1906.

Figure 20:
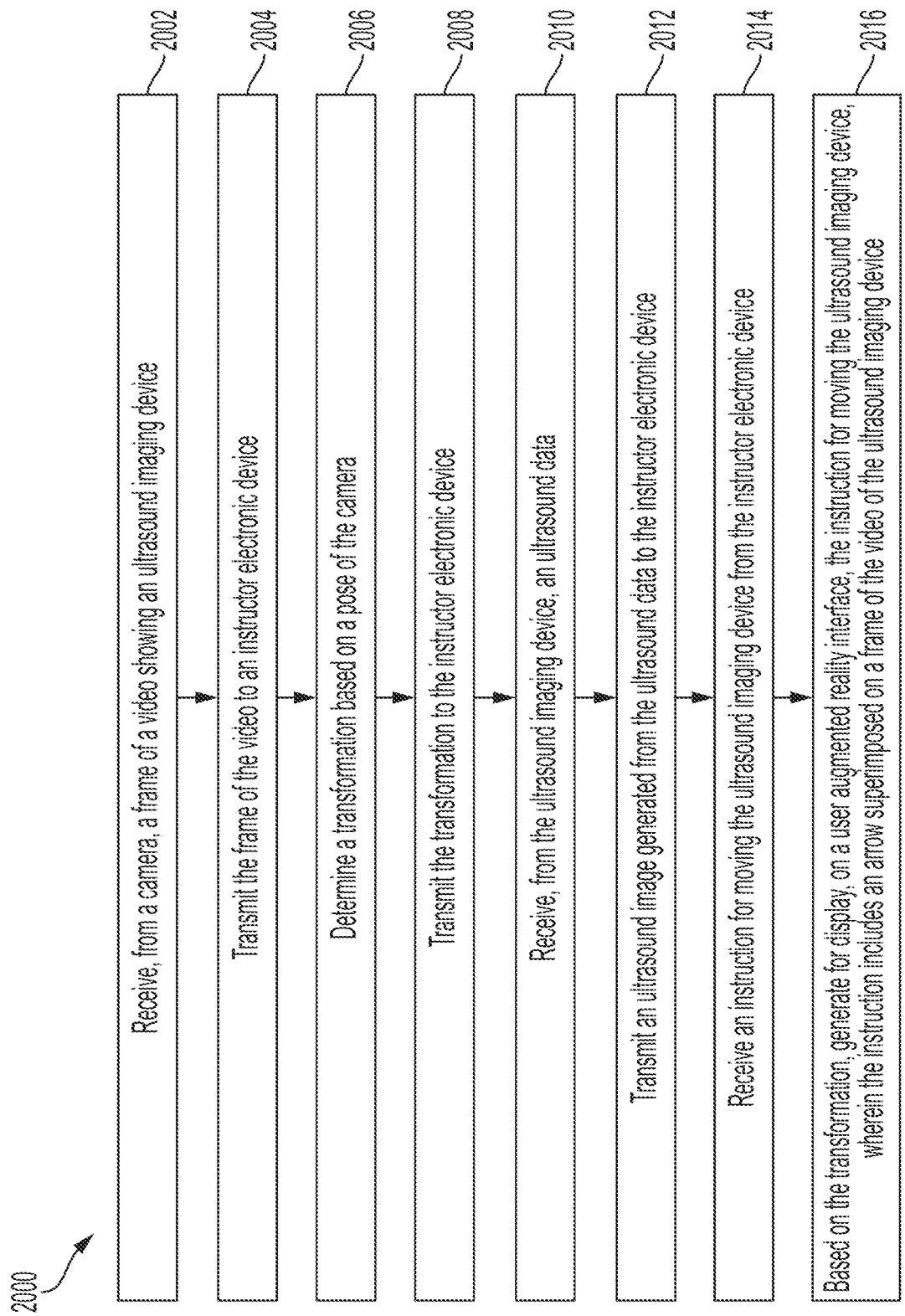
FIG. 20 shows an example process for tele-medicine executable by a user electronic device, in accordance with an exemplary embodiment.

FIG. 20 shows an example process 2000 for tele-medicine executable by a user electronic device (e.g., user electronic device 102), in accordance with an exemplary embodiment. The user electronic device may be associated with a user of an ultrasound imaging device (e.g., ultrasound imaging device 114). The user electronic device may be in communication (e.g., over a wired or wireless connection) with the ultrasound imaging device and in communication (e.g., over a wireless connection) with an instructor electronic device (e.g., instructor electronic device 122) associated with an instructor who is providing instructions to the user of the ultrasound imaging device. The user electronic device and the instructor electronic device may be remote from each other.

In act 2002, the user electronic device receives, using a camera (e.g., camera 106), a frame of a video (e.g., the frame of the video 610) showing the ultrasound imaging device. For example, if the user electronic device is a mobile phone, the camera may be the mobile phone's camera. The user of the ultrasound imaging device may hold the ultrasound imaging device on a subject being imaged and position the camera of the user electronic device (which the user may also be holding) such that the ultrasound imaging device is in view of the camera. In some embodiments, the user electronic device may continuously capture video throughout the ultrasound imaging session. The process 2000 proceeds from act 2002 to act 2004.

In act 2004, the user electronic device transmits the frame of the video captured in act 2002 to the instructor electronic device. The user electronic device may encode the video as any suitable form of data for transmission. In some embodiments, the user electronic device may transmit the video to the instructor electronic device over a wireless communication link (e.g., over a BLUETOOTH, WiFi, or ZIGBEE wireless communication link). In embodiments in which the user electronic device continuously captures video, the user electronic device may continuously transmit frames of the video to the instructor electronic device throughout the imaging session. The process 2000 proceeds from act 2004 to act 2006.

In act 2006, the user electronic device determines a transformation from the frame of the video captured in act 2002. The user electronic device may use pose estimation techniques to determine the transformation. The transformation may include a quantification of translations, rotations, and/or tilts of the camera from the default pose to the current pose, and may be in the form of a matrix. The user electronic device may use pose estimation techniques to analyze a particular frame of the video from a particular time to determine the transformation at the particular time. In embodiments in which the instructor electronic device continuously receives frames of the video, the instructor electronic device may continuously receive updated transformations based on the current frame of the video throughout the imaging session. The process 2000 proceeds from act 2006 to 2008.

In act 2008, the user electronic device transmits the transformation determined in in act 2006 to the instructor electronic device. The user electronic device may encode the transformation as any suitable form of data for transmission. In some embodiments, the user electronic device may transmit the transformation to the instructor electronic device over a wireless communication link (e.g., over a BLUETOOTH, WiFi, or ZIGBEE wireless communication link). In embodiments in which the user electronic device continuously determines transformations, the user electronic device may continuously transmit transformations to the instructor electronic device throughout the imaging session. The process 2000 proceeds from act 2008 to act 2010.

In act 2010, the user electronic device receives ultrasound data from the ultrasound imaging device. In some embodiments, the ultrasound imaging device may collect raw ultrasound data, transmit the raw ultrasound data to the user electronic device, and the user electronic device may generate an ultrasound image (e.g., ultrasound image 502) from the raw ultrasound data. In some embodiments, the ultrasound imaging device may collect raw ultrasound data, generate the ultrasound image from the raw ultrasound data, and transmit the ultrasound image to the user electronic device. The user electronic device may receive the ultrasound data from the ultrasound imaging device over a wired connection, for example, through a lightning connector or a mini-USB connector. The process 2000 proceeds from act 2010 to act 2012

In act 2012, the user electronic device transmits the ultrasound image to the instructor electronic device. In some embodiments, the user electronic device may transmit the ultrasound image to the instructor electronic device over a wireless communication link (e.g., over a BLUETOOTH, WiFi, or ZIGBEE wireless communication link). When new ultrasound data is collected and a new ultrasound image is generated, the user electronic device may transmit the new ultrasound image to the instructor electronic device. The process 2000 proceeds from act 2012 to act 2014.

In act 2014, the user electronic device receives an instruction from the instructor electronic device for moving the ultrasound imaging device. Instructions for moving the ultrasound imaging device may include any combination of instructions to translate the ultrasound imaging device, instructions to rotate the ultrasound imaging device (i.e., rotation about the longitudinal axis of the ultrasound imaging device), and instructions to tilt the ultrasound imaging device (e.g., tilting the ultrasound imaging device about the end portion of the ultrasound imaging device contacting the subject). The instructions to move the ultrasound imaging device may be instructions designed to move the ultrasound imaging device from a current position to a position and orientation on a subject such that a target anatomical view (e.g., a parasternal long axis view of the heart) can be obtained.

As discussed above with reference to FIG. 19, in some embodiments the instructor electronic device may receive a selection of an arrow from a plurality of arrows shown on an instructor AR interface, where each of the arrows corresponds to a possible instruction for moving the ultrasound imaging device. By selecting the arrow, the instructor may decide that the user should move the ultrasound imaging device in a direction indicated by the arrow in order to move the ultrasound imaging device closer to the target anatomical region. As further discussed above with reference to FIG. 19, in some embodiments, each of the arrows shown in the instructor AR interface may have an identifier, and the instructor electronic device may transmit the identifier of the selected arrow to the user electronic device. For example, consider an arrow that points right in a default pose of the camera relative to the ultrasound imaging device. As discussed above, as the pose of the camera relative to the ultrasound imaging device changes, the instructor AR interface may generate for display the arrow, using the transformation, in different directions as seen in the video so that the direction of the arrow relative to the ultrasound imaging device may remain substantially constant. At any given time, however, the arrow may be identified as the "right" arrow, based on its direction as seen in the video in the default pose, despite the arrow not necessarily pointing to the right as seen in the video at the given time. If the arrow identified as "right" is selected at the instructor electronic device, the user electronic device may receive the instruction corresponding to this arrow by receiving the identifier "right" from the instructor electronic device. In other words, the identifier may include a description of the arrow as seen in the default pose of the camera relative to the ultrasound imaging device. The process 2000 proceeds from act 2014 to 2016.

In act 2016, based on the transformation, the user electronic device generates for display, on a user augmented reality (AR) interface (e.g., user AR interface 1100) shown on the user electronic device, the instruction (received in act 2014) for moving the ultrasound imaging device. The instruction as shown in the user AR interface includes an arrow superimposed on a frame of the video. (The frame of the video may be the same frame of the video received in act 2002, or if a new frame of the video has been received between acts 2002 and 2014, a new frame of the video). The arrow may indicate translation, rotation, and/or tilting of the ultrasound imaging device. As discussed above, in some embodiments, the instruction received by the user electronic device may include an identifier of the arrow selected on the instructor interface. In such embodiments, to generate the arrow for display on the user AR interface, the user electronic device may determine, based on the identifier, the direction of the arrow from the perspective of the camera in the default pose of the camera. For example, the user electronic device may look up, in a database, the direction of the arrow corresponding to the received identifier from the perspective of the camera in the default pose of the camera. The user electronic device may then use the transformation to determine how to change the direction of the arrow (e.g., rotation and/or tilting) from the perspective of the camera such that the arrow is shown in the user AR interface as pointing in substantially the same direction from the perspective of the ultrasound imaging device that they would in the default pose.

It should be noted that the acts of process 2000 may not necessarily proceed in the order shown in FIG. 20. For example, act 2004 may occur after act 2006, act 2008 may occur before or simultaneously with act 2004, and acts 2010 and 2012 may occur before or simultaneously with acts 2002, 2004, 2006, and 2008.

In some embodiments, the ultrasound image collected by the ultrasound imaging device and shown on the instructor interface at a time when an instruction for moving the ultrasound imaging device is selected by the instructor may be saved to memory (e.g., on the servers 134) and associated with the selected instruction. Pairs of ultrasound images and instructions saved in this way may be used to train a model (e.g., a deep learning model/statistical model) to automatically determine, based on an inputted ultrasound image, an instruction for moving an ultrasound imaging device. Such a model may be used to automatically instruct a user, based on ultrasound images collected by an ultrasound imaging device, how to move the ultrasound imaging device to a position and orientation where a target anatomical view can be collected. For further discussion of deep learning/machine learning techniques and automated acquisition assistance, see U.S. patent application Ser. No. 15/626,423 titled "AUTOMATIC IMAGE ACQUISITION FOR ASSISTING A USER TO OPERATE AN ULTRASOUND DEVICE," filed on Jun. 19, 2017 (and assigned to the assignee of the instant application), which is incorporated by reference herein in its entirety.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A system, comprising:
an ultrasound imaging device;
a user electronic device comprising a camera and a display screen, the user electronic device physically separate from and electronically connectable to the ultrasound imaging device; and
an instructor electronic device including an instructor augmented reality interface, the instructor electronic device in communication with the user electronic device, wherein the instructor augmented reality interface includes (a) a video of the ultrasound image device captured by and communicated from the user electronic device and (b) a plurality of selectable arrows superimposed on the video, each of the plurality of selectable arrows corresponding to an instruction to translate, rotate, or tilt the ultrasound imaging device,
wherein the user electronic device is configured to:
receive, from the instructor electronic device, an instruction for moving the ultrasound imaging device;
display, on a user augmented reality interface included on the user electronic device, the instruction for moving the ultrasound imaging device;
receive, from the instructor electronic device, a selection to change an imaging parameter for the ultrasound imaging device;
based on the received selection to change the imaging parameter, generate a command to change the imaging parameter for the ultrasound imaging device;
transmit, to the ultrasound imaging device, the command to change the imaging parameter for the ultrasound imaging device;

receive, from the instructor electronic device, an instruction to freeze an ultrasound image on the display screen of the user electronic device; and based on the received instruction to freeze the ultrasound image, cease updating the ultrasound image on the display screen of the user electronic device.

2. The system of claim 1, wherein the user electronic device is further configured to:

receive a video captured by the camera, the video depicting the ultrasound imaging device; and wherein:

the user augmented reality interface comprises the video depicting the ultrasound imaging device.

3. The system of claim 2, wherein the user electronic device is configured, when displaying the instruction on the user augmented reality interface, to display an arrow superimposed on the video showing the ultrasound imaging device.

4. The system of claim 3, wherein the ultrasound imaging device comprises one or more fiducial markers.

5. The system of claim 4, wherein the user electronic device is further configured to:

determine a first transformation from a default pose of the camera relative to the one or more fiducial markers to a first pose of the camera relative to the one or more fiducial markers at a first time; and display the user augmented reality interface based on the first transformation.

6. The system of claim 5, wherein the user electronic device is further configured to:

determine a second transformation from the default pose of the camera relative to the one or more fiducial markers to a second pose of the camera relative to the one or more fiducial markers at a second time after the first time, wherein the first transformation is different from the second transformation; and display the user augmented reality interface based on the second transformation.

7. The system of claim 4, wherein the user electronic device is further configured to display the arrow in a direction that appears in the user augmented reality interface to be normal to one of the one or more fiducial markers.

8. The system of claim 4, wherein the user electronic device is further configured to display the arrow such that the arrow appears in the user augmented reality interface to form a circular path parallel to a plane of one of the one or more fiducial markers.

9. The system of claim 4, wherein the user electronic device is further configured to display the arrow such that the arrow appears in the user augmented reality interface to form a circular path orthogonal to a plane of one of the one or more fiducial markers.

10. The system of claim 1, wherein the instructor electronic device is operated by an instructor.

11. The system of claim 1, wherein the user electronic device is further configured to:

receive an instruction to stop moving the ultrasound imaging device; and display, on the user electronic device, the instruction to stop moving the ultrasound imaging device.

12. The system of claim 1, wherein the user electronic device is further configured to:

receive an instruction to stop moving the ultrasound imaging device; and cease to display, on the user augmented reality interface included on the user electronic device, the instruction for moving the ultrasound imaging device.

13. The system of claim 1, wherein the user electronic device is further configured to:

receive, from the instructor electronic device, a selection to change an imaging preset; and change the imaging preset.

14. The system of claim 1, wherein the user electronic device is further configured to:

receive, from the instructor electronic device, a selection to change an imaging gain; and change the imaging gain.

15. The system of claim 1, wherein the user electronic device is further configured to:

receive, from the instructor electronic device, a selection to change an imaging depth; and change the imaging depth.

16. The system of claim 1, wherein the user electronic device is further configured to:

receive, from the instructor electronic device, a selection to save one or more ultrasound images to memory; and save the one or more ultrasound images to memory.

17. The system of claim 1, wherein the user electronic device is further configured to:

receive an instruction to move the ultrasound imaging device into a particular anatomical region; and display the instruction to move the ultrasound imaging device into the particular anatomical region.

18. The system of claim 1, wherein the user electronic device is further configured to:

receive, from the instructor electronic device, an instruction to instruct a subject to take and hold a deep breath; and display the instruction to instruct the subject to take and hold a deep breath.

19. The system of claim 1, wherein the user electronic device is further configured to:

receive an instruction to move the ultrasound imaging device into view of the camera; and display the instruction to move the ultrasound imaging device into view of the camera.

20. The system of claim 1, wherein the user electronic device is further configured to:

receive, from the instructor electronic device, an instruction to press the ultrasound imaging device harder onto a subject; and display the instruction to press the ultrasound imaging device harder onto the subject.

21. The system of claim 1, wherein the user electronic device is further configured to:

receive an instruction to move the ultrasound imaging device in at least one of shorter or smaller increments; and display the instruction to move the ultrasound imaging device in at least one of shorter or smaller increments.

22. The system of claim 1, wherein the user electronic device is further configured to:

transmit, to the instructor electronic device, ultrasound data collected by at least one of the ultrasound imaging device or an ultrasound image generated from the ultrasound data.

23. The system of claim 1, wherein the selection to change the imaging parameter for the ultrasound imaging device comprises a selection to change at least one of an imaging preset, an imaging gain, or an imaging depth for the ultrasound imaging device.

24. The system of claim 1, wherein the user electronic device is a mobile smartphone, the mobile smartphone comprises the camera, and the wire is flexible, configured to mate with the user electronic device and configured to facilitate electronic communication between the user electronic device and the ultrasound imaging device.

* * * * *